(12) United States Patent
Takekoshi et al.

(10) Patent No.: US 9,036,945 B2
(45) Date of Patent: May 19, 2015

(54) MEDICAL IMAGE HANDLING SYSTEM AND METHOD

(75) Inventors: Koji Takekoshi, Kanagawa (JP); Akira Tago, Tokyo (JP); Makoto Sato, Tokyo (JP); Keiichi Sakai, Kanagawa (JP); Tsukasa Sako, Kanagawa (JP); Kazuhiko Takahashi, Kanagawa (JP); Muling Guo, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/296,821

(22) Filed: Nov. 15, 2011

(65) Prior Publication Data

US 2012/0069048 A1 Mar. 22, 2012

Related U.S. Application Data

(62) Division of application No. 12/972,901, filed on Dec. 20, 2010, now abandoned, which is a division of application No. 10/714,654, filed on Nov. 18, 2003, now Pat. No. 7,965,907.

(30) Foreign Application Priority Data

Nov. 21, 2002 (JP) .................................. 2002-338380
Mar. 17, 2003 (JP) .................................. 2003-071853

(51) Int. Cl.
G06K 9/54 (2006.01)
G06K 9/60 (2006.01)
H04N 1/00 (2006.01)
G06Q 10/00 (2012.01)
A61B 5/00 (2006.01)
G06F 3/048 (2013.01)
G06F 3/00 (2006.01)

(Continued)

(52) U.S. Cl.
CPC ................ *G06Q 10/10* (2013.01); *G06Q 50/22* (2013.01); *G06Q 50/24* (2013.01)

(58) Field of Classification Search
None
See application file for complete search history.

(56) References Cited

U.S. PATENT DOCUMENTS 4,339,799 A * 7/1982 Abele et al. ...................... 378/11
5,235,510 A    8/1993 Yamada et al. ................ 600/300

(Continued)

FOREIGN PATENT DOCUMENTS

CN    1283289    2/2001
CN    2446953    9/2001

(Continued)

OTHER PUBLICATIONS

Office Action issued Sep. 29, 2013 by PRC State Intellectual Property Office in counterpart Chinese Patent Application 200510109246.3, with partial translation.

(Continued)

*Primary Examiner* — Randolph I Chu
(74) *Attorney, Agent, or Firm* — Fitzpatrick, Cella, Harper & Scinto

(57) ABSTRACT

A medical image handling system includes a monitor for displaying a medical image, an input device for inputting an image reading report corresponding to the medical image displayed on the monitor, and a processor. The processor judges the presence or absence of an image reading report corresponding to the medical image displayed on the monitor, and restricts a change of the medical image in a case where the image reading report is judged as being absent.

10 Claims, 24 Drawing Sheets

(51) Int. Cl.
*G06Q 10/10* (2012.01)
*G06Q 50/22* (2012.01)
*G06Q 50/24* (2012.01)

(56) References Cited

U.S. PATENT DOCUMENTS

| | | | | |
|---|---|---|---|---|
| 5,752,030 | A | 5/1998 | Konno et al. | 718/102 |
| 5,779,634 | A * | 7/1998 | Ema et al. | 600/407 |
| 5,954,650 | A * | 9/1999 | Saito et al. | 600/425 |
| 5,991,429 | A | 11/1999 | Coffin et al. | 382/118 |
| 6,039,047 | A * | 3/2000 | Rock et al. | 128/897 |
| 6,188,402 | B1 | 2/2001 | Csipkes et al. | 715/705 |
| 6,343,137 | B1 | 1/2002 | Kimura et al. | 382/100 |
| 6,434,569 | B1 | 8/2002 | Toshimitsu et al. | 707/100 |
| 6,498,486 | B1 * | 12/2002 | Ookawa | 324/312 |
| 6,504,960 | B2 | 1/2003 | Takahashi | 382/305 |
| 6,789,087 | B1 | 9/2004 | Sako | 707/999.005 |
| 6,822,676 | B1 | 11/2004 | Kurosawa et al. | 348/211.3 |
| 7,119,841 | B1 * | 10/2006 | Sako | 348/333.05 |
| 7,174,515 | B1 * | 2/2007 | Marshall et al. | 715/763 |
| 2001/0007593 | A1 * | 7/2001 | Oosawa | 382/132 |
| 2002/0072417 | A1 | 6/2002 | Kudo | 463/43 |
| 2002/0099569 | A1 | 7/2002 | Thirsk | 705/2 |
| 2002/0158875 | A1 * | 10/2002 | Yamada | 345/440 |
| 2002/0193676 | A1 * | 12/2002 | Bodicker et al. | 600/407 |
| 2003/0007674 | A1 | 1/2003 | Tsujii et al. | 382/132 |
| 2003/0045796 | A1 * | 3/2003 | Friedman | 600/450 |
| 2003/0055317 | A1 | 3/2003 | Taniguchi et al. | 600/117 |
| 2003/0095150 | A1 * | 5/2003 | Trevino et al. | 345/810 |
| 2004/0062421 | A1 | 4/2004 | Jakubowski et al. | 382/115 |
| 2006/0271403 | A1 * | 11/2006 | Iwasa et al. | 705/2 |

FOREIGN PATENT DOCUMENTS

| | | |
|---|---|---|
| CN | 1331454 | 1/2002 |
| JP | 08-076741 | 3/1996 |
| JP | 08-256991 | 10/1996 |
| JP | 2001-157667 | 6/2001 |

OTHER PUBLICATIONS

Japanese Office Action issued Dec. 14, 2010 in counterpart Japanese Application No. 2008-256991, with translation.

* cited by examiner

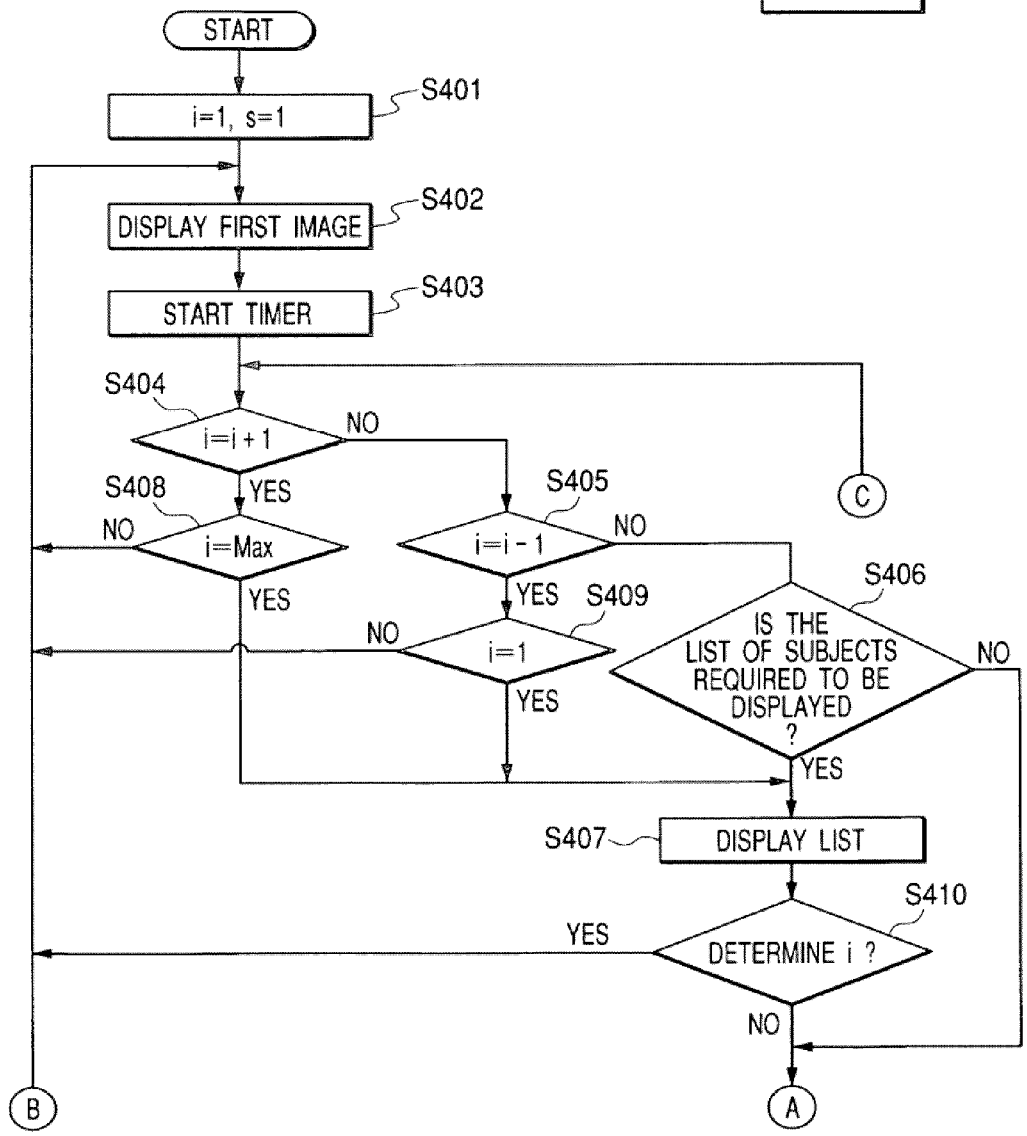

FIG. 18

| PATIENT NAME | DIVIDED DISPLAY FORMAT | | PRIORITY NOT-DIVIDED | PRIORITY DIVIDED INTO TWO | PRIORITY DIVIDED INTO FOUR |
|---|---|---|---|---|---|
| PATIENT A (NEXT) | INSPECTION 1 | SERIES 1 | 1 | 1 | 1 |
| | | SERIES 2 | 2 | 3 | 5 |
| | | SERIES 3 | 3 | 4 | 6 |
| | INSPECTION 2 | SERIES 1 | | 2 | 2 |
| | | SERIES 2 | | | |
| | INSPECTION 3 | SERIES 1 | | | 3 |
| | INSPECTION 4 | SERIES 1 | | | 4 |
| | | SERIES 2 | | | |
| | | SERIES 3 | | | |

FIG. 19

| PATIENT NAME | | PRIORITY | |
|---|---|---|---|
| DIVIDED DISPLAY FORMAT | | LEFT: TAKEN IMAGE<br>RIGHT: TAKEN IMAGE | DIVIDED INTO TWO<br>LEFT: TAKEN IMAGE<br>RIGHT: DIAGNOSIS SUPPORTING IMAGE |
| PATIENT A<br>(NEXT) | INSPECTION 1 | 1 | 1 |
| | INSPECTION 2 | 2 | 3 |
| | INSPECTION 3 | 4 | 4 |
| | INSPECTION 4 | 5 | 5 |
| | CAD<br>INSPECTION 1-<br>INSPECTION 2 | 3 | 2 |
| | CAD<br>INSPECTION 2-<br>INSPECTION 3 | 6 | 6 |
| | CAD<br>INSPECTION 3-<br>INSPECTION 4 | 7 | 7 |

MEDICAL IMAGE HANDLING SYSTEM AND METHOD

RELATED APPLICATIONS

This is a divisional of application Ser. No. 12/972,901, filed Dec. 20, 2010, which is a divisional of application Ser. No. 10/714,654, filed Nov. 18, 2003 (now U.S. Pat. No. 7,965, 907, issued Jun. 21, 2011), claims benefit of both of those applications under 35 U.S.C. §120, and claims priority benefit under 35 U.S.C. §119 from Japanese Patent Applications Nos. 2002-338380, filed Nov. 21, 2002, and 2003-071853, filed Mar. 17, 2003. The entire contents of each of the four mentioned applications are incorporated herein by reference.

BACKGROUND OF THE INVENTION

1. Field of the Invention

The present invention relates to a medical image handling system and a medical image handling method for a medical X-ray image or the like.

2. Related Background Art

For an X-ray photographing for example for medical diagnosis, there is often utilized a film-screen system in which a sensitizing screen and an X-ray photographic film are combined.

In such system, X-rays transmitted by an object include internal information of the object, and are converted by the sensitizing screen into visible light proportional to the intensity of the X-rays. Then the thus-converted visible light exposes the X-ray photographic film to form an X-ray image thereon.

In a medical facility utilizing such a system, the X-ray image is conventionally observed by placing the film on a light box.

On the other hand, there is recently being employed a digital X-ray image pickup apparatus capable of reading a radiation image as an electrical signal and executing a digital conversion of the read electrical signal to a digital image by various methods, such as a method of accumulating an X-ray intensity distribution as a latent image of energy in a stimulable phosphor and reading that image, a method of directly reading a fluorescence distribution of a fluorescent member formed by the X-rays, or a method of reading an image by a technology not utilizing the fluorescence distribution.

Also, because digital image pickup has become possible, digital image diagnosis by displaying the obtained image on a display screen of a computer instead of outputting such image on a film, is beginning to be used.

On the other hand, in the medical imaging field, there has recently been active investigation of computer aided diagnosis (CAD), which analyzes a simple X-ray image or a computerized tomography (CT) image by a computer to generate a CAD image (diagnosis assisting image) and detecting from such CAD image (diagnosis assisting image) a portion suspected for a disease, and which is expected to contribute to early detection of diseases.

SUMMARY OF THE INVENTION

An aspect of the present invention is to judge the presence or absence of a diagnosis report on a medical image displayed on a monitor, and to restrict a change in the medical image displayed on the monitor, in a case where it is judged that the diagnosis report is absent.

Another aspect of the present invention is to judge, in a case where a medical image displayed on a monitor is changed to a medical image of another subject, whether there exists another medical image different from the one currently displayed on the monitor but belonging to the subject of the medical image displayed on the monitor, and to restrict a change of subject in a case where there exists another, different medical image belonging to the subject of the medical image displayed on the monitor.

Still other aspects of the present invention will become fully apparent from following description to be taken in conjunction with accompanying drawings.

BRIEF DESCRIPTION OF THE DRAWINGS

FIG. 18 shows the fifth embodiment and is a view indicating an example of a priority of prefetching order in case of displaying a picked-up image;

FIG. 19 shows the fifth embodiment and is a view indicating an example of a priority of prefetching order in case of displaying two images in laterally divided two image display areas;

DESCRIPTION OF THE PREFERRED EMBODIMENTS

In the following, embodiments of the medical image handling system of the present invention will be explained with reference to FIGS. 1 to 7.

First Embodiment

Figure 1:
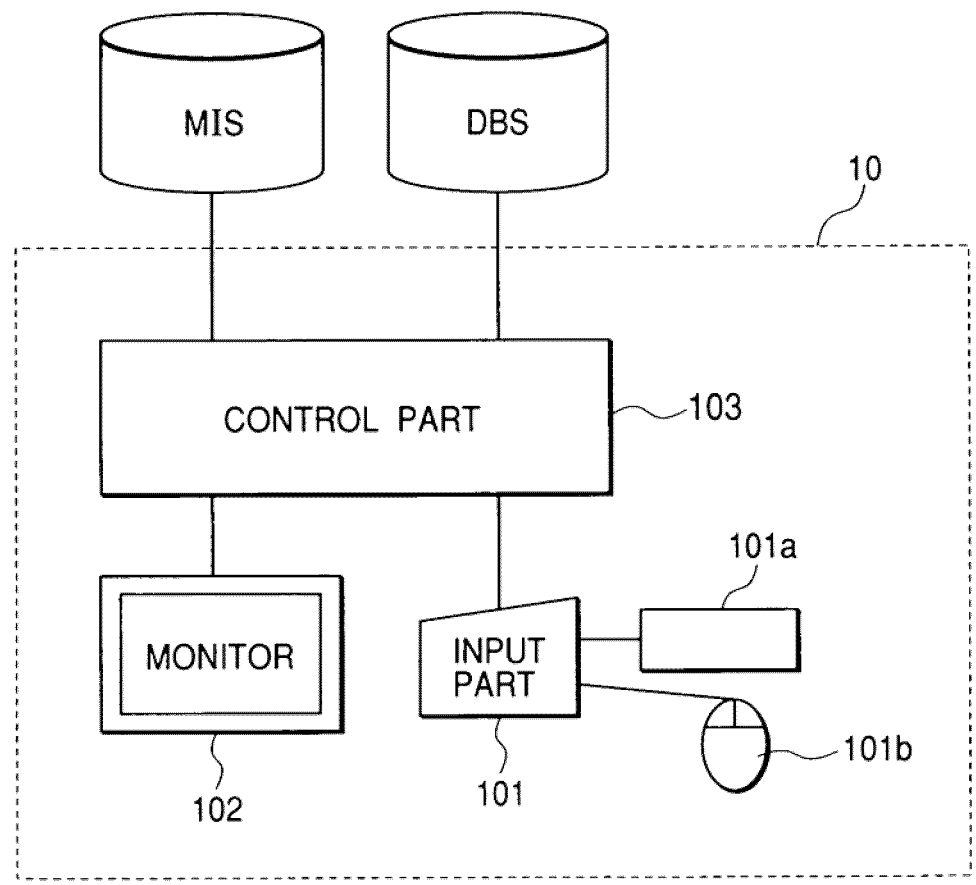
FIG. 1 is a block diagram of a medical image handling system of a first embodiment.

A medical image handling system 10 of a first embodiment of the present invention is provided, as shown in FIG. 1, with an input part 101 such as a keyboard 101a and a mouse 101b, a monitor 102 for displaying a dialog image or a medical image, and a control part 103 provided with a recording medium storing programs for controlling a communication with a medical image server (MIS) and a database server (DBS) and the entire medical image handling system 10.

Figure 2:
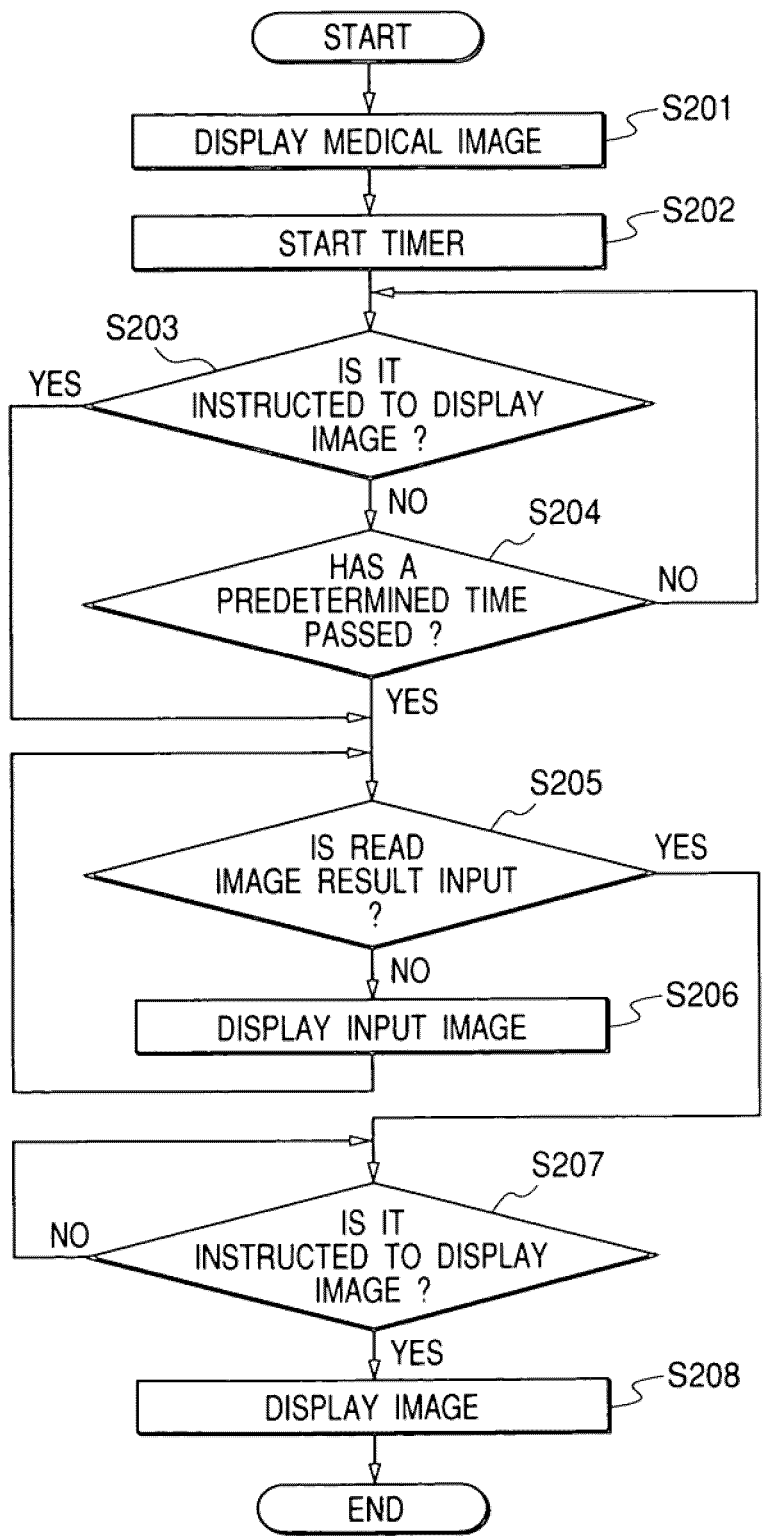
FIG. 2 is a flow chart showing a function of the medical image handling system of the first embodiment.

In the following, there will be given an explanation on how the control part 103 controls the medical image handling system 10, with reference to a flow chart shown in FIG. 2.

In step S201, in response to an input from the keyboard 101a or the mouse 101b, the control part 103 executes a control for communicating with the medical image server (MIS) and transferring a desired medical image for display on the monitor 102.

Then step S202 starts a timer in order to count a display time of the medical image displayed in step S201. Usually a person who reads an image (hereinafter referred to as "an image reading person") starts image reading of the desired medical image after the medical image is displayed on the monitor 102, beginning a period of waiting for the end of the image reading after the timer is started.

Step S203 discriminates the presence or absence of an operation for displaying an image other than the medical image displayed in step S201. When the image reading person completes the reading of the medical image displayed in step S201, there is executed, on the keyboard 101a or the mouse 101b, an operation for displaying another medical image or displaying an image for example of a list of patients. This step discriminates the presence or absence of such operation. Thus the image reading of the currently displayed medical image is judged to have been completed by such operation for displaying an image different from the currently displayed medical image. The sequence proceeds to step S205 in a case where step S203 identifies the presence of an operation for displaying an image other than the current medical image, but proceeds to step S204 in the absence of such operation.

Step S204 discriminates whether a predetermined display time has elapsed for the display of the medical image since the start of time counting in step S202. If the predetermined time has elapsed, the sequence proceeds to step S205, but, if not, the sequence returns to step S203.

Step S205 discriminates whether an image reading result has been entered in an image reading result report. The sequence proceeds to step S207 or S206 respectively in the case where an image reading result is entered or not in the image reading result report. In the case of an image displayed for the first time, the sequence always proceeds to step S206 because there is no entry of the result in the image reading result report.

Step S206 displays an image for entering an image reading result report. The image reading person enters a result of the image reading for the medical image displayed in step S201, utilizing the keyboard 101a and the mouse 101b. The entered image reading result report is stored in the database server (DBS).

The image for entering the image reading result report is so constructed that a document of a fixed pattern including an image reading result to be entered can be selected from a pull-down menu, in order to achieve an efficient input operation.

Also, in preparation for a case that a document of a fixed pattern is insufficient, there is prepared an image for entering detailed information, thereby enabling to enter detailed information such as a name of a disease and a history thereof in the image reading result report.

Also, in case of a collective inspection of a group of subjects, it is usual that abnormality is not found in most of the subjects. Therefore, in the absence of an abnormality, an input simpler than the pull-down menu is also possible by a single click of a button.

Also, it is possible to suspend the preparation of an image reading result report, in case the report cannot be prepared at the present stage and is to be prepared later by reading the image again.

Step S207 discriminates, like step S203, the presence or absence of an operation for displaying an image other than the medical image displayed in step S201. Stated differently, there is awaited an operation for displaying an image other than the currently displayed medical image. Once such operation occurs, the sequence proceeds to step S208, but this step is repeated in the absence of such operation.

Step S208 displays, based on the operation in step S207, an image other than the medical image displayed in step S201.

As explained in the foregoing, in the case of displaying another medical image other than the medical image displayed in step S201, there is executed a control necessitating an input in the image for entering the image reading result report, whereby an omission of the input of the image reading result can be prevented.

The input of the image reading result is not limited to a keyboard or a mouse, but can also be executed by another input device or by a voice input.

Second Embodiment

Figure 3:
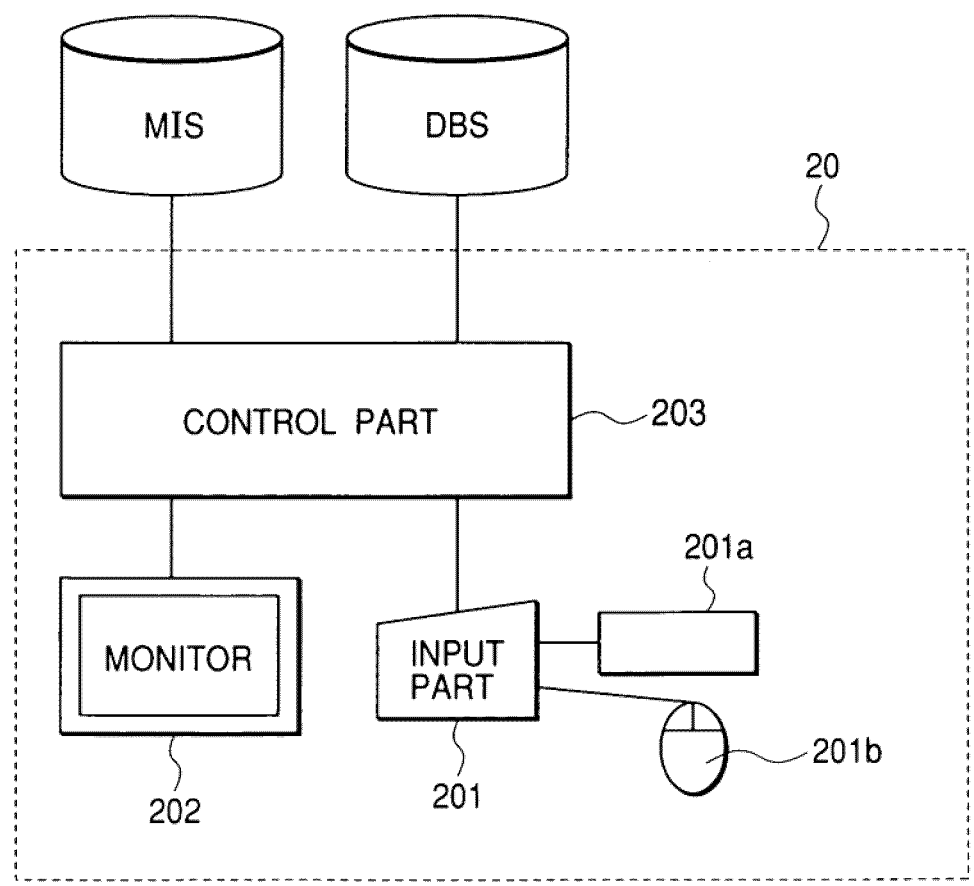
FIG. 3 is a block diagram of a medical image handling system of a second embodiment.

A medical image handling system 20 of a second embodiment of the present invention is provided, as shown in FIG. 3, with an input part 201 such as a keyboard 201a and a mouse 201b, a monitor 202 for displaying a dialog image or a medical image, and a control part 203 provided with a recording medium storing programs for controlling a communication with a medical image server (MIS) and a database server (DBS) and the entire medical image handling system 20.

Figure 4:
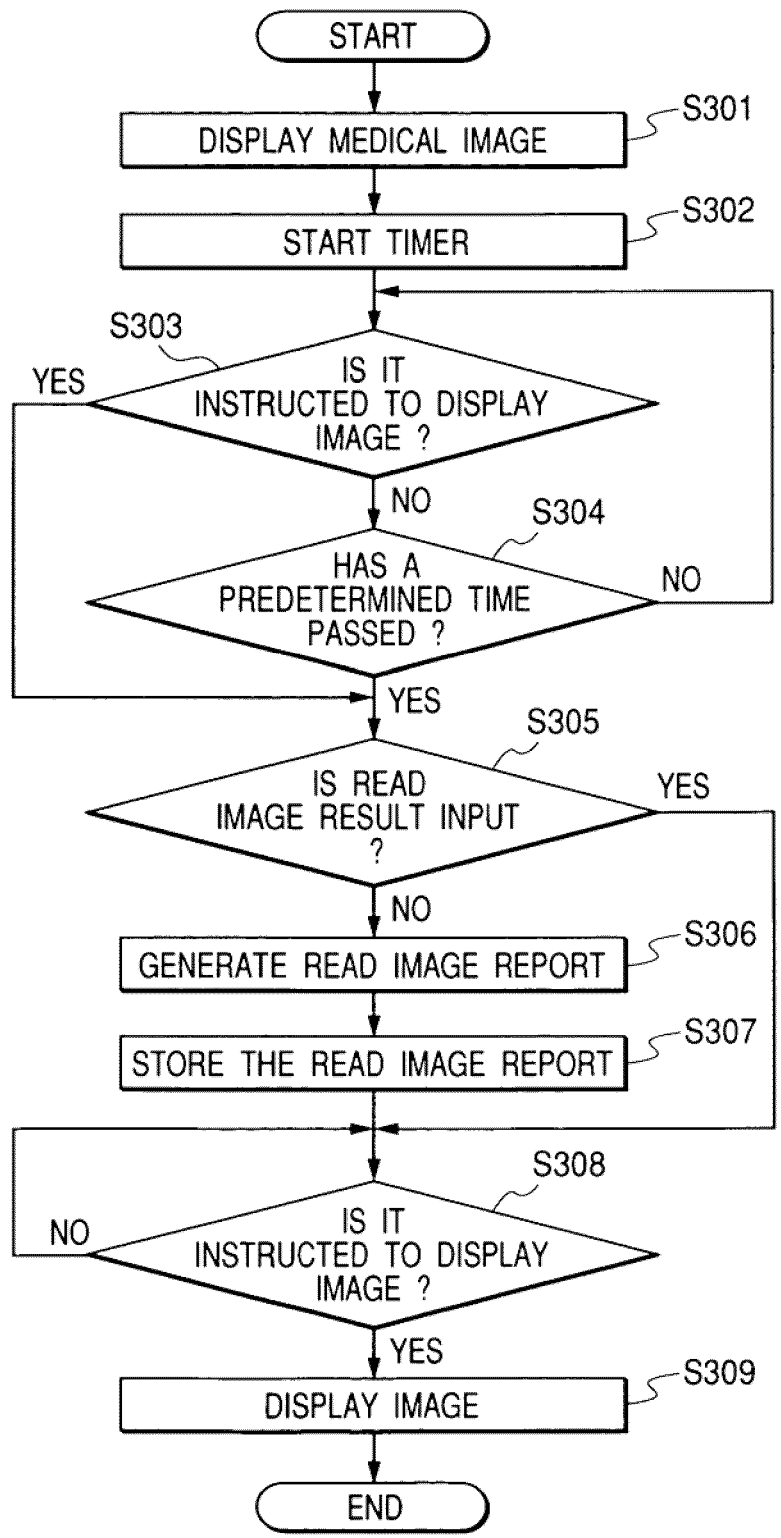
FIG. 4 is a flow chart showing a function of the medical image handling system of the second embodiment.

In the following, there will be given an explanation on how the control part 203 controls the medical image handling system 20, with reference to a flow chart shown in FIG. 4.

In step S301, in response to an input from the keyboard 201a or the mouse 201b, the control part 203 executes a control for communicating with the medical image server (MIS) and transferring a desired medical image for display on the monitor 202.

Then step S302 starts a timer in order to count a display time of the medical image displayed in step S301. Usually an image reading person starts image reading of the desired medical image after the medical image is displayed on the monitor 202, beginning a period of waiting for the end of the image reading after the timer is started.

Step S303 discriminates the presence or absence of an operation for displaying an image other than the medical image displayed in step S301. When the image reading person completes the reading of the medical image displayed in step S301, there is executed, on the keyboard 201a or the mouse 201b, an operation for displaying another medical image or displaying an image for example of a list of patients. Thus the image reading of the currently displayed medical image is judged to have been completed by such operation for displaying an image different from the currently displayed medical image.

The sequence proceeds to step S305 in a case where step S303 identifies that there has been an operation for displaying an image other than the current medical image, but proceeds to step S304 in the absence of such operation.

Step S304 discriminates whether a predetermined display time has elapsed for the display of the medical image since the start of time counting in step S302. If the predetermined time has elapsed, the sequence proceeds to step S305, but, if not, the sequence returns to step S303.

Step S305 discriminates whether an image reading result has been entered in an image reading result report. The sequence proceeds to step S307 or S306 respectively according as an image reading result is entered or not in the image reading result report. In a case of an image being displayed for the first time, the sequence always proceeds to step S306 because there is no entry of the result in the image reading result report.

Step S306 automatically generates an image reading result report. A content of the automatically generated image reading result report can be set in advance. Since there is often prepared a report indicating the absence of any abnormal observation, there is set "no observation".

In this operation, there are automatically entered a display time of the image as a time required for image reading, and a name of the image reading person in the image reading result report. Upon generation of the image reading result report, the sequence proceeds to step S307.

Step S307 stores the image reading result report, generated in step S306, in the database server DBS. After the storage of the image reading result report, the sequence proceeds to step S308.

Step S307 discriminates, like step S303, the presence or absence of an operation for displaying an image other than the medical image displayed in step S201. Stated differently, there is awaited an operation for displaying an image other than the currently displayed medical image. In the presence of such operation, there is displayed an image other than the currently displayed medical image, but this step is repeated in the absence of such operation.

As explained above, the present embodiment displays a medical image, and generates an image reading result report automatically in case the image reading result report is not entered after the lapse of a predetermined time.

The input of the image reading result is not limited to a keyboard or a mouse, but can also be executed by another input device or by a voice input.

Third Embodiment

Figure 5:
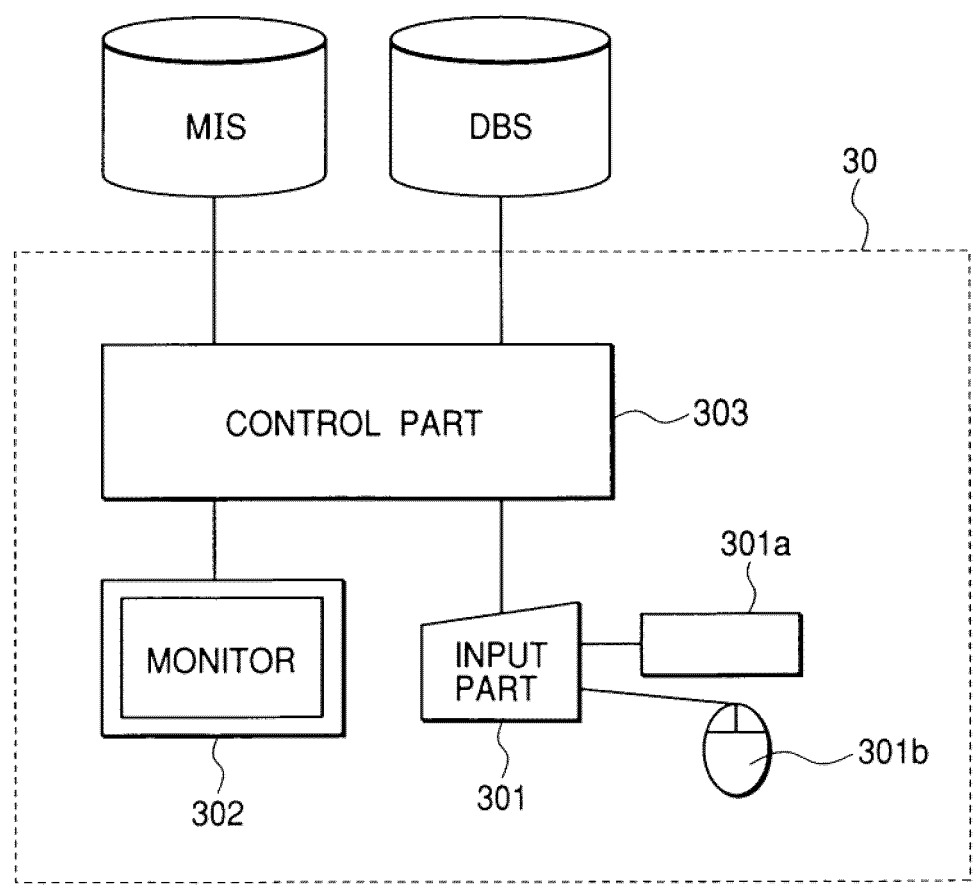
FIG. 5 is a block diagram of a medical image handling system of a third embodiment.

A medical image handling system 30 of a third embodiment of the present invention is provided, as shown in FIG. 5, with an input part 301 such as a keyboard 301a and a mouse 301b, a monitor 302 for displaying a dialog image or a medical image, and a control part 303 provided with a recording medium storing programs for controlling a communication with a medical image server (MIS) and a database server (DBS) and the entire medical image handling system 30.

Figure 6:
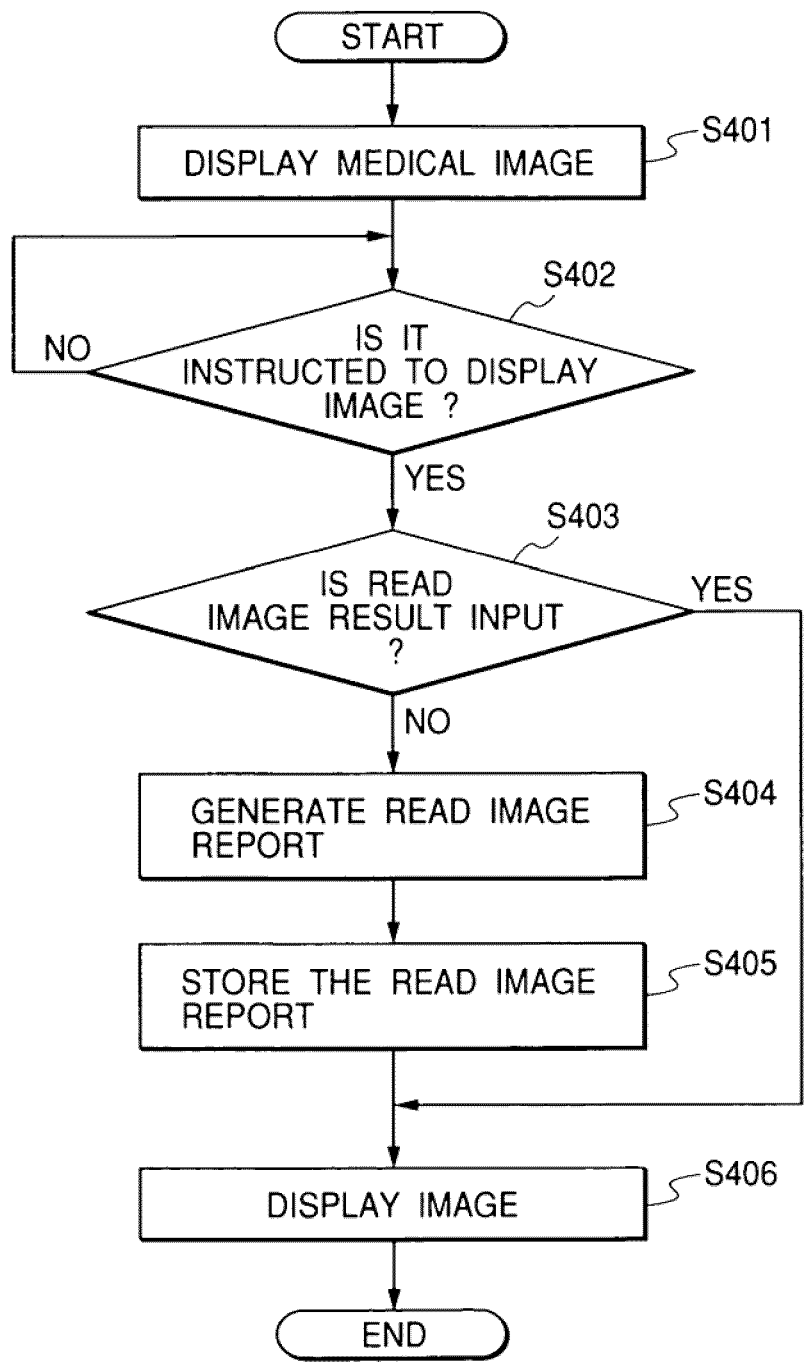
FIG. 6 is a flow chart showing a function of the medical image handling system of the third embodiment.

In the following, there will be given an explanation on how the control part 303 controls the medical image handling system 30, with reference to a flow chart shown in FIG. 6.

In step S401, in response to an input from the keyboard 301a or the mouse 301b, the control part 303 executes a control for communicating with the medical image server (MIS) and transferring a desired medical image for display on the monitor 302.

Step S402 discriminates presence or absence of an operation for displaying an image other than the medical image displayed in step S401. When the image reading person completes the reading of the medical image displayed in step S401, there is executed, on the keyboard 301a or the mouse 301b, an operation for displaying another medical image or displaying an image for example of a list of patients. Thus the image reading of the currently displayed medical image is judged to have been completed by such operation for displaying an image different from the currently displayed medical image.

Step S403 discriminates whether an image reading result has been entered in an image reading result report. The sequence proceeds to step S406 or S404 respectively according as an image reading result is entered or not in the image reading result report. In a case of an image being displayed for the first time, the sequence always proceeds to step S404 because there is no entry of the result in the image reading result report.

Step S404 automatically generates an image reading result report. A method of automatic generation of the image reading result report is similar to that in the second embodiment and will not be explained further. Upon generation of the image reading result report, the sequence proceeds to step S405.

Step S405 stores the image reading result report, generated in step S404, in the database server DBS. After the storage of the image reading result report, the sequence proceeds to step S406.

Step S406 executes an image display corresponding to the operation in step S402. For example, if step S402 executes an operation for displaying a medical image of a next subject, step S406 displays the medical image of the next subject. Also, if step S402 executes an operation of displaying a list of medical images, step S406 displays the list of the medical images.

As explained above, the present embodiment displays a medical image, then, in the case of an operation for displaying an image other than the displayed medical image, there is discriminated presence or absence of an input of an image reading result report, generates an image reading result report automatically in case the image reading result report is not entered.

The input of the image reading result is not limited to a keyboard or a mouse, but can also be executed by another input device or by a voice input.

Variation of Third Embodiment

Figure 7:
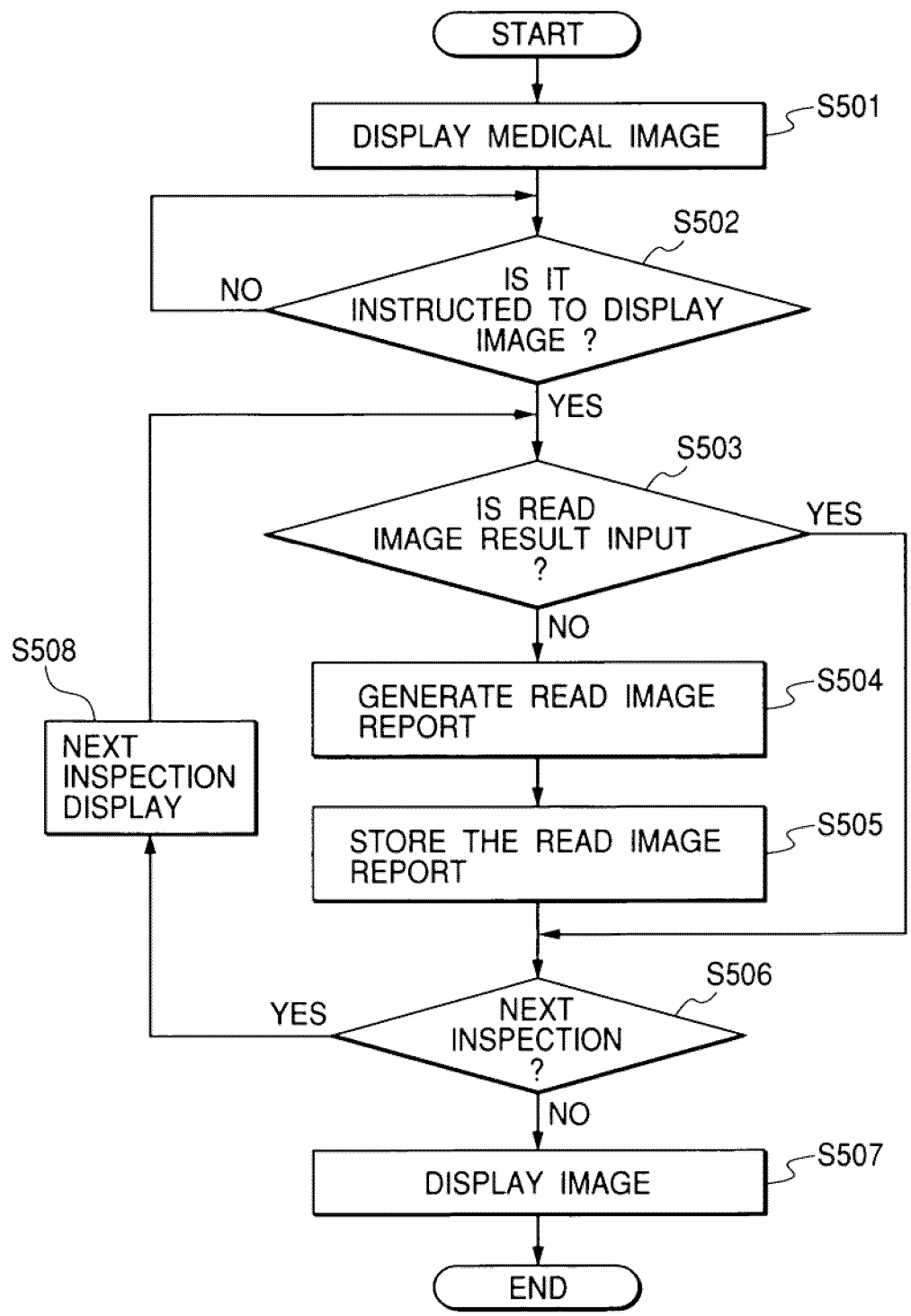
FIG. 7 is a flow chart showing a function of a medical image handling system constituting a variation of the third embodiment.

FIG. 7 is a flow chart showing a case in the foregoing third embodiment where a subject waits for plural inspections.

An inspection is defined by the DICOM standard and is from the start of an image taking operation to the end thereof. For example, in case of taking a chest X-ray image, an image of the chest part is taken from the start of an image taking operation, and the image taking operation is thus terminated. In this case, there will be provided a chest X-ray image for an inspection.

In step S501, in response to an input from the keyboard 301a or the mouse 301b, the control part 303 executes a control for communicating with the medical image server (MIS) and transferring a desired medical image for display on the monitor 302.

Step S502 discriminates presence or absence of an operation for displaying an image other than the medical image displayed in step S501. When the image reading person completes the reading of the medical image displayed in step S501, there is executed, on the keyboard 301a or the mouse 301b, an operation for displaying another medical image or displaying an image for example of a list of patients. Thus the image reading of the currently displayed medical image is judged to have been completed by such operation for displaying an image different from the currently displayed medical image.

Step S503 discriminates whether an image reading result has been entered in an image reading result report. The sequence proceeds to step S506 or S504 respectively according as an image reading result is entered or not in the image reading result report. In a case of an image being displayed for the first time, the sequence always proceeds to step S504 because there is no entry of the result in the image reading result report.

Step S504 automatically generates an image reading result report. A method of automatic generation of the image reading result report is similar to that in the second embodiment and will not be explained further. Upon generation of the image reading result report, the sequence proceeds to step S505.

Step S505 stores the image reading result report, generated in step S504, in the database server DBS. After the storage of the image reading result report, the sequence proceeds to step S506.

Step S506 discriminates whether there is a next inspection for the currently displayed subject. Since the monitor displays an image of a latest inspection of the subject, if step S501 instructs the display of an image taken at 10:10 a.m., Apr. 1, 2002, the "next inspection" mentioned above means an inspection taken before 10:10 a.m. Apr. 1, 2002.

In a case where there is an inspection taken before the date of the medical image displayed in step S501, for example an inspection taken at 11:40 a.m., Mar. 1, 2001, the sequence proceeds to step S508, but, in a case where there is no inspection taken before the date of the medical image displayed in step S501, the sequence proceeds to step S507.

Step S508 displays a medical image of an inspection taken before the date of the medical image displayed in step S501, and the sequence proceeds to step S503. For example, a medical image of an inspection taken at 11:40 a.m., Mar. 1, 2001, is displayed and the sequence proceeds again to step S503. Thereafter, the sequence proceeds to step S507 when the next sequences are exhausted.

Step S507 executes an image display corresponding to an operation content in step S502.

Fourth Embodiment

Figure 8:
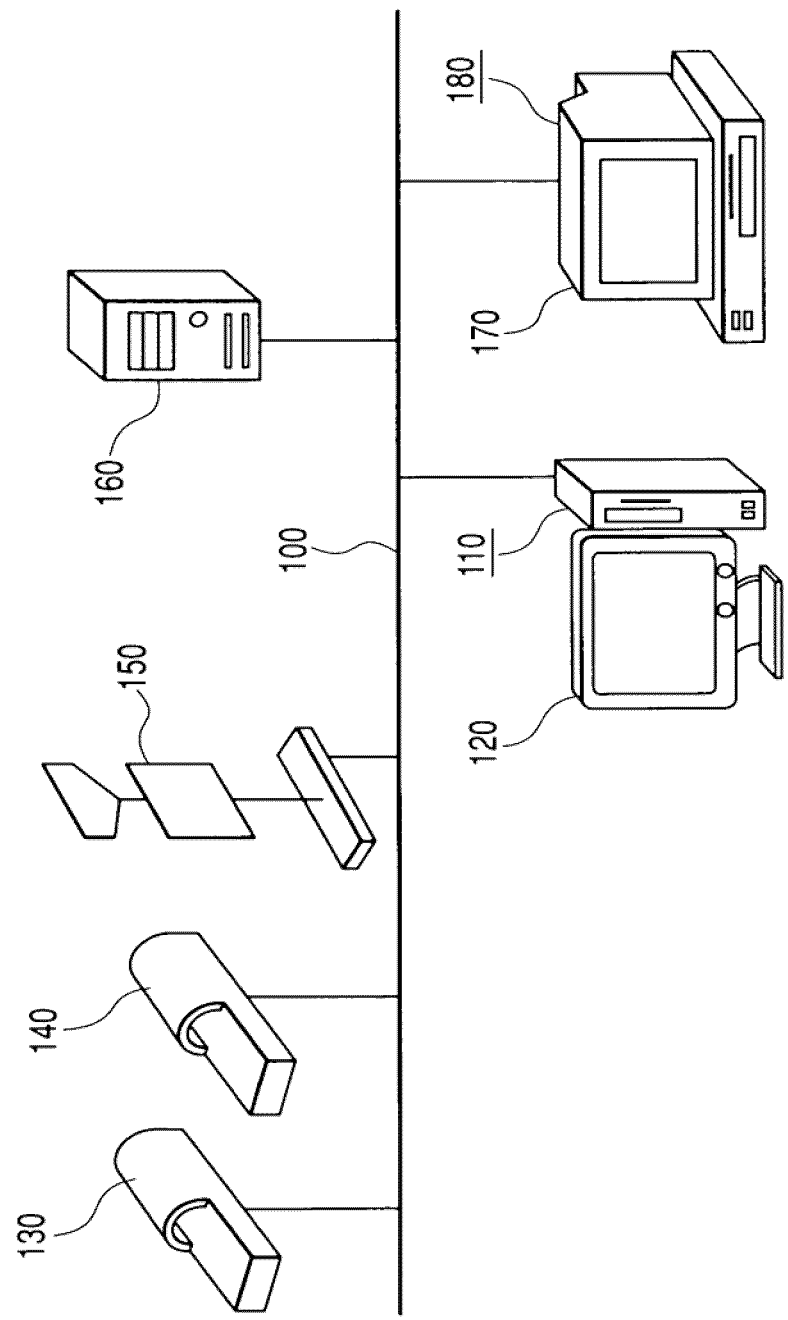
FIG. 8 is a schematic view showing a comprehensive medical system including a medical image handling system and constituting a fourth embodiment.
Figure 9:
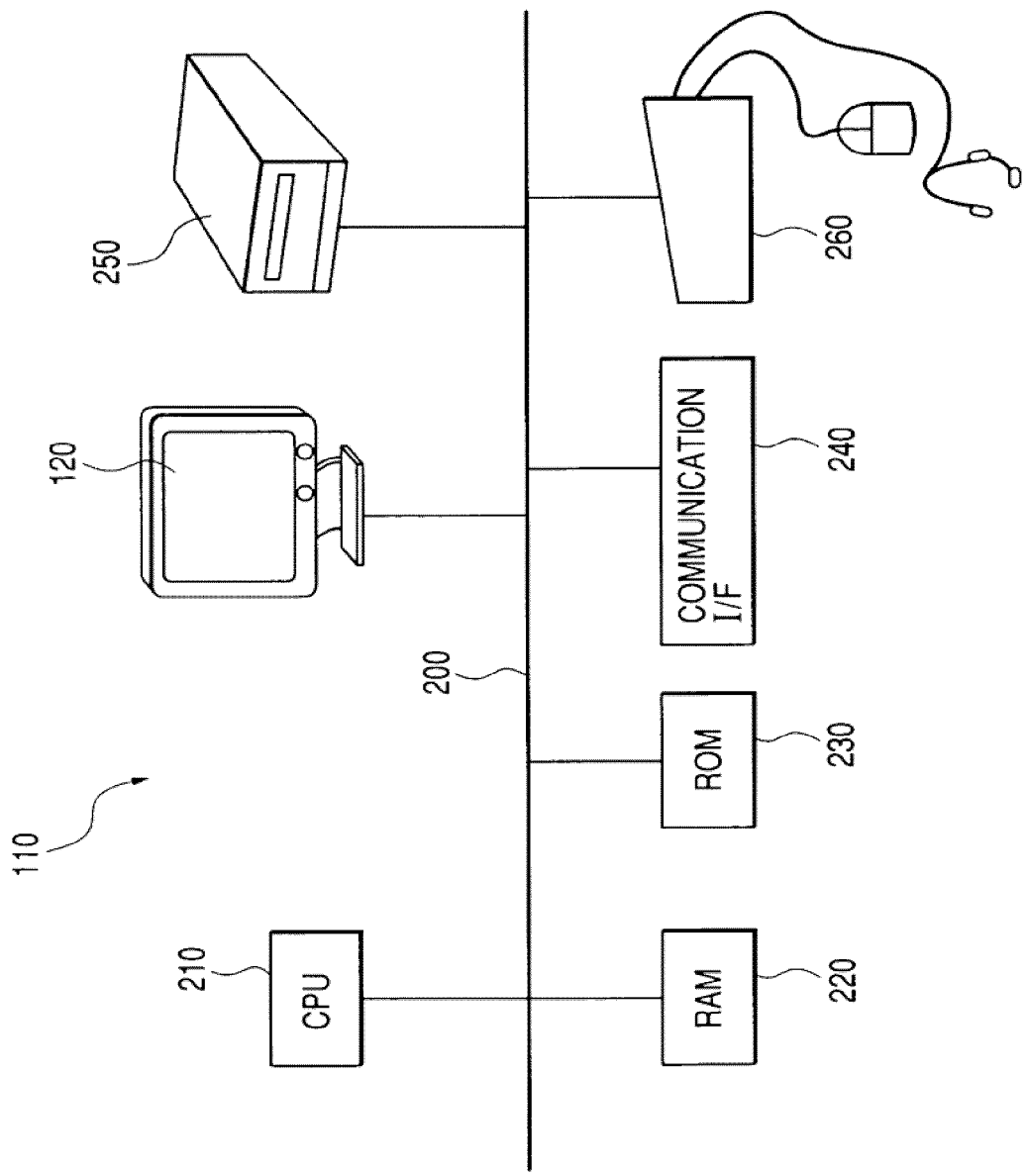
FIG. 9 is a block diagram of a medical image handling system of a fourth embodiment.
Figure 10:
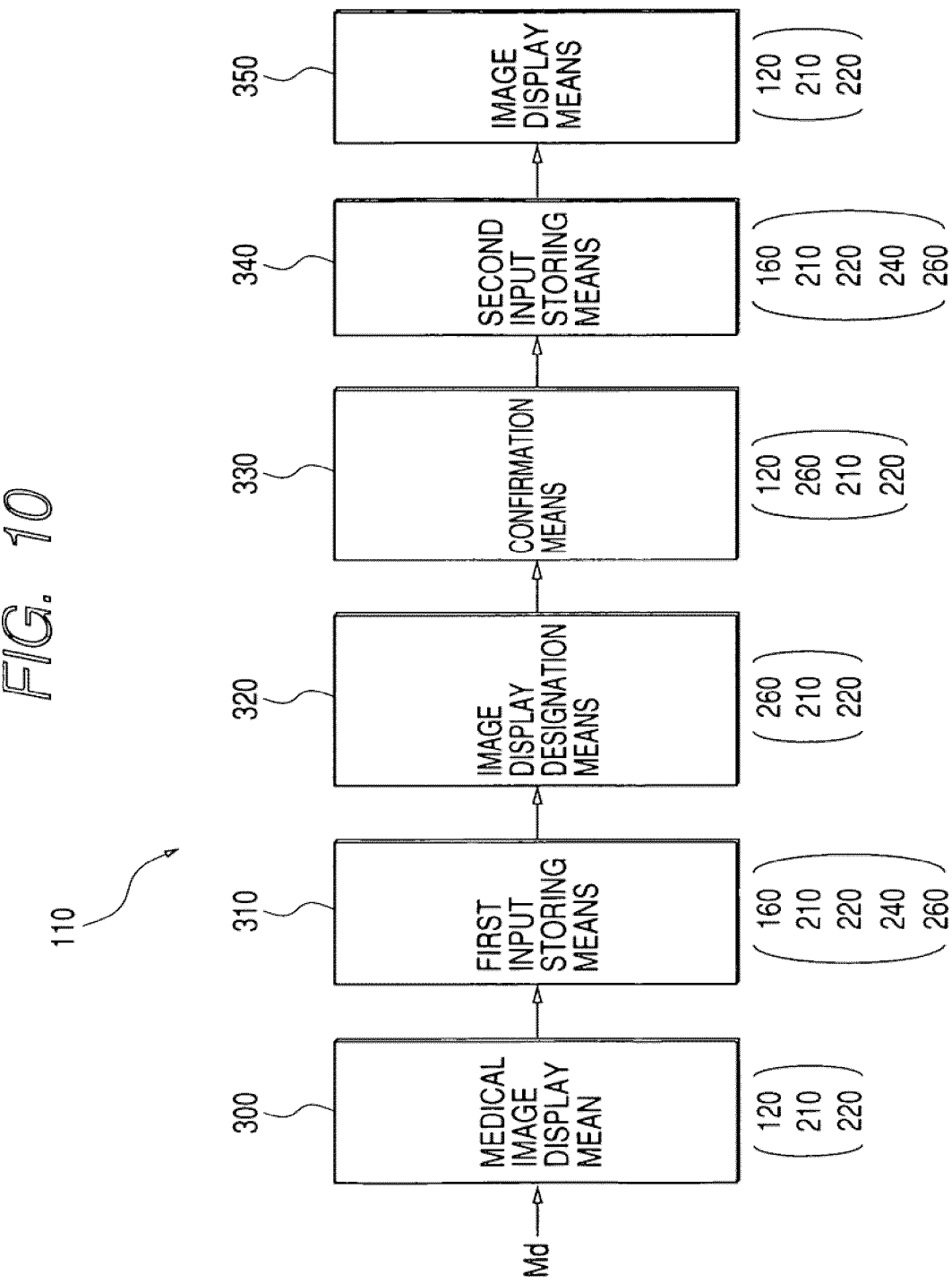
FIG. 10 is a functional block diagram showing a function of the medical image handling system of the fourth embodiment.

FIG. 8 is a view showing an entire comprehensive medical system including a medical image handling system and constituting a fourth embodiment, FIG. 9 is a block diagram showing an internal configuration of the medical image handling system, and FIG. 10 is a functional block diagram showing a function of the medical image handling system.

Referring to FIG. 8, a medical image handling system 110 is connected, through a local area network (LAN) 100, to medical image generating apparatuses 130, 140, 150 and a medical data server 160. The medical image generating apparatuses 130, 140 are for example a CT scan apparatus and an MRI apparatus, and the medical image generating apparatus 150 is for example an X-ray image pickup apparatus.

Medical images generated in the medical image generating apparatuses 130, 140, 150 are transmitted, either directly or through the medical data server 160, to the medical image handling system 110. The medical image transmitted directly to the medical image handling system 110 is stored in a memory medium thereof.

The medical image handling system 110 is provided with a general-purpose color liquid crystal monitor 120, thereby being capable of easily displaying a medical image. There can also be utilized a medical image handling system 180 provided with a monochromatic medical image monitor 170 of a higher definition.

In response to an instruction of an image reading person, the medical image handling system 110 displays the received medical image, and the image reading person can read the medical image and enter a result of such image reading in the medical image handling system 110.

Referring to FIG. 9, the medical image handling system 110 is formed by connecting, to a bus 200, a CPU 210, a RAM 220, a ROM 230, a communication interface 240 and input means 260, and output apparatuses such as general-purpose color liquid crystal monitor 120, a printer 250, etc., are connected to the bus 200 through an appropriate interface. The input means includes a keyboard, a pointing device, a microphone etc.

The CPU 210 is used for controlling the entire medical image handling system 110 and the output apparatuses, and a control program therefor is stored in the ROM 230. A communication interface 240 controls a communication by the LAN 100, and exchanges medical image and other data with the medical image generating apparatuses 130, 140, 150 and the medical data server 160.

Referring to FIG. 10, the medical image handling system 110, upon receiving medical data Md including a medical image, displays the medical image and other medical data by a medical image handling system 300 (corresponding to the general-purpose color liquid crystal monitor 120 in FIG. 8 and the CPU 210 and the RAM 220 in FIG. 9). The image reading person reads the medical image and enters and stores a result of image reading by first input storage means 310 (corresponding to the medical data server 160 in FIG. 8 and the CPU 210, the RAM 220, the communication interface 240 and the input means 260 in FIG. 9).

The first input storage means 310 is capable of a process of suspending the input of the result of image reading, and, in such case, the medical data record that the result of image reading is not recorded but suspended. In this manner the image reading person can enter the result of image reading at an arbitrary timing and can avoid a lapse in recording.

Such suspension is effective for example in a case of browsing an entire collection of images as in a slide show, in a case of screening by an image reading, in a case where a judgment is not easy, in a case where a second reading later is desirable, or in a case where an input is intentionally not desired.

The medical data once stored can be displayed again by image display designation means 320 (corresponding to the input means 260, CPU 210 and RAM 220 in FIG. 9), and the image reading person can confirm the medical data by confirmation means 330 (corresponding to the general-purpose color liquid crystal monitor 120 in FIG. 8 and the input means 260, CPU 210 and RAM 220 in FIG. 9). For the redisplayed medical image, a result of image reading can be entered or edited by second input storage means (corresponding to the medical data server 160 in FIG. 8 and the CPU 210, RAM 220, communication interface 240 and input means 260 in FIG. 9). The medical image after such input and editing is displayed, under a condition designated by the image display designation means 320, in image display means 350 (corresponding to the general-purpose color liquid crystal monitor 120 in FIG. 8 and the CPU 210 and the RAM 220 in FIG. 9).

Presence of such second input storage means allows the image reading person to record the result of image reading at an arbitrary timing.

It is also possible to limit the medical image that can be redisplayed, to a medical image for which the result of image reading is suspended. In this manner such suspended medical image can be automatically extracted, thereby avoiding a lapse in the record.

In the following there will be explained a medical image reading method to be executed in the medical image handling system 110.

Figure 11B:
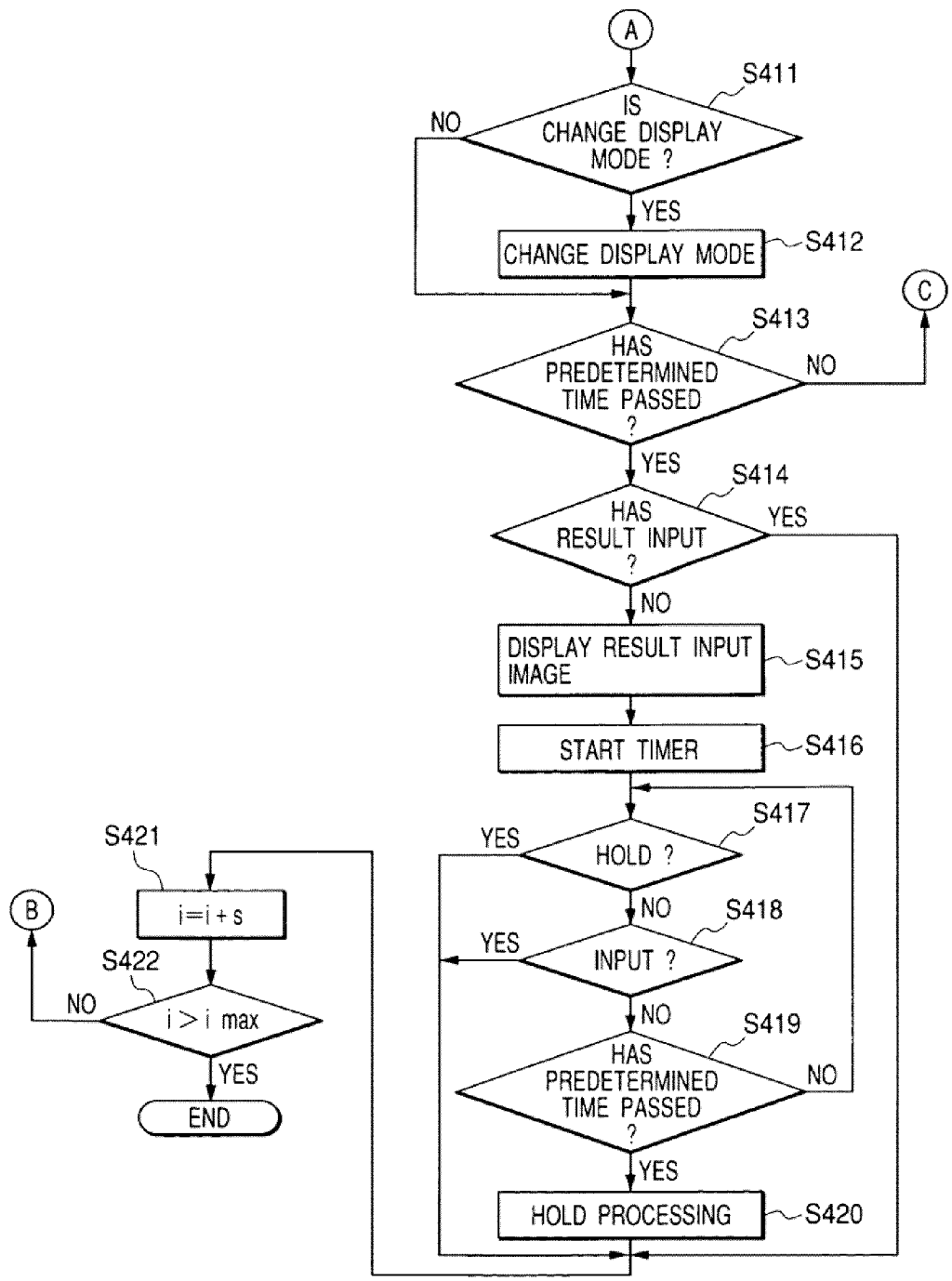
FIG. 11 is comprised of FIGS. 11A and 11B showing flow charts illustrating a function of the medical image handling system of the fourth embodiment.
Figure 12:
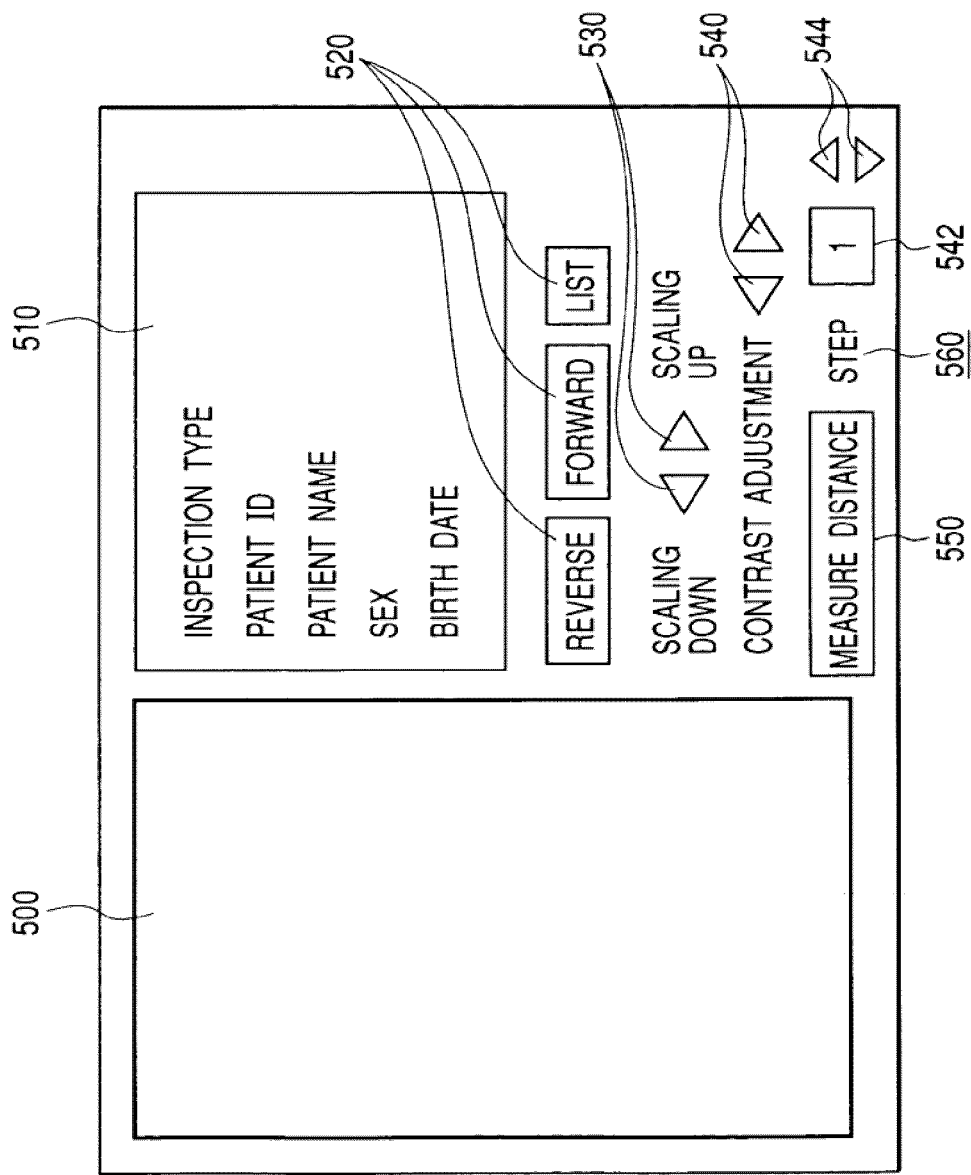
FIG. 12 is a view showing a medical image display frame in the medical image handling system of the fourth embodiment.
Figure 13:
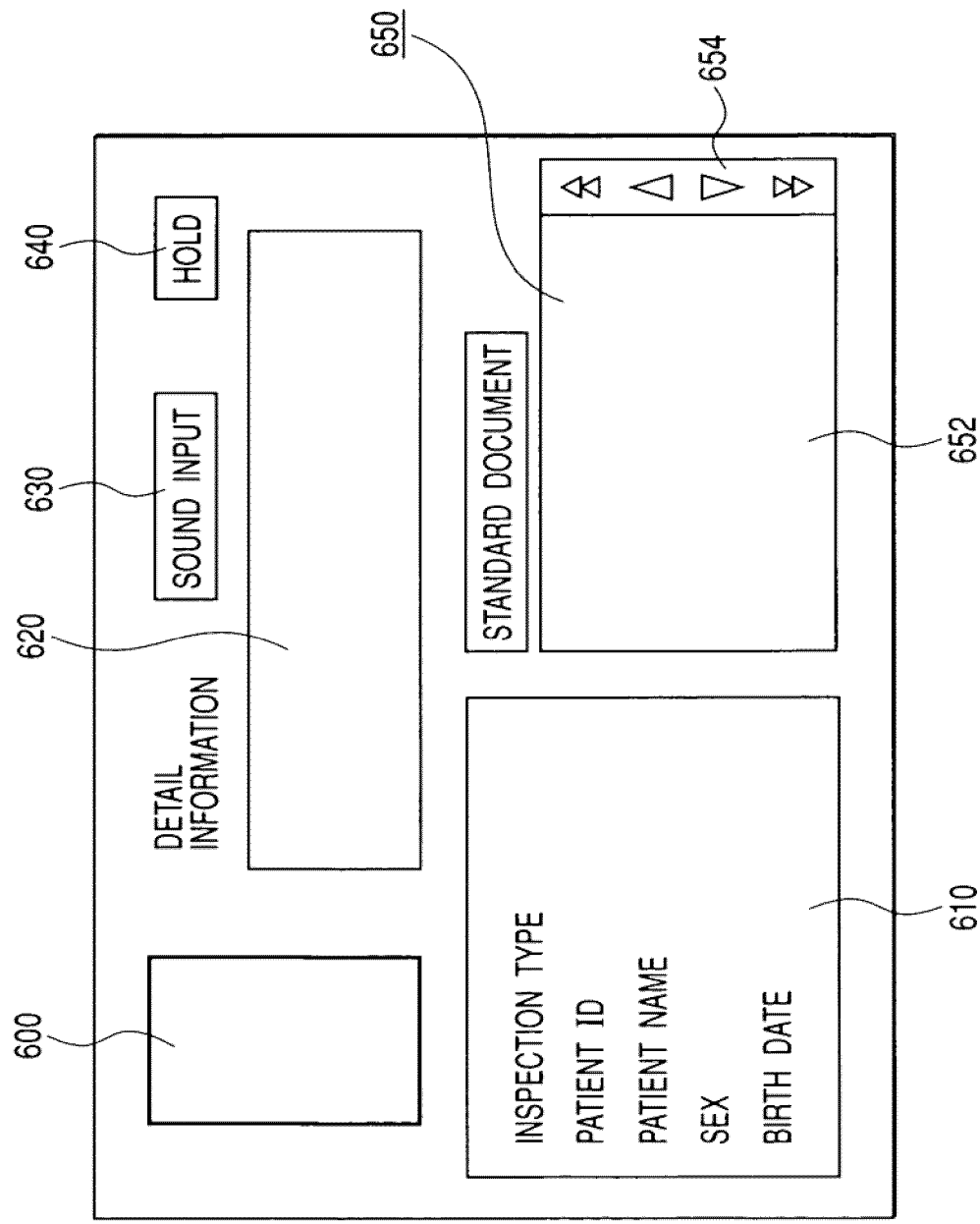
FIG. 13 is a view showing a diagnosis result input image in the medical image handling system of the fourth embodiment.
Figure 14:
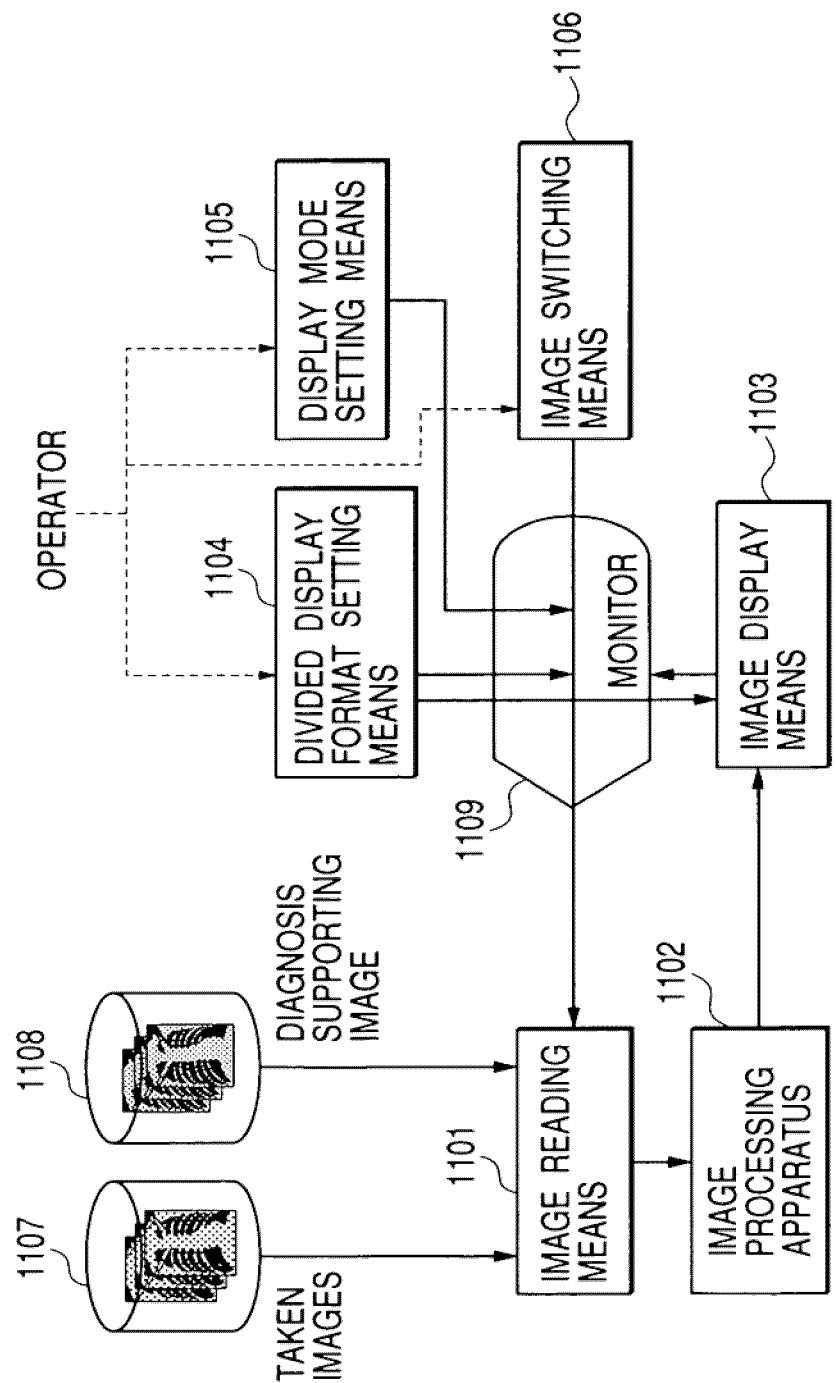
FIG. 14 shows a fifth embodiment and is a block diagram showing an example of a configuration of a medical image handling system.

FIGS. 11A and 11B are flow charts showing a process in the fourth embodiment of the medical image processing method, FIG. 12 is an elevation view showing a medical image display frame in the fourth embodiment, FIG. 13 is an elevation view showing an image reading result entering image in the fourth embodiment, and FIG. 14 is a conceptual view showing a data structure of the medical data in the fourth embodiment.

A medical image reading method shown in a flow chart in FIGS. 11A and 11B are executed in the following manner:

Step S401: It is assumed that an image is displayed for each subject, and a subject number "i" corresponding to the medical image and an interval (step) "s" of the displayed medical images are set at a default value "1". In this manner the medical images are displayed in succession from a first image. Then the sequence proceeds to step S402.

Step S402: An i-th medical image is displayed on the general-purpose color liquid crystal monitor 120.

As shown in FIG. 12, the general-purpose color liquid crystal monitor 120 displays a medical image display area 500, a subject data display area 510, an instruction 520 for image designation, instructions 530, 540, 550 for a display mode change, and a step designation area 560. The subject data display area 510 displays a patient ID, patient name, sex and birth date of a subject corresponding to the medical image. These are based on the DICOM standard.

Then the sequence proceeds to step S403:

Step S403: a timer is started in order to count an image reading time. Then the sequence proceeds to step S404:

Step S404: There is discriminated whether the image reading person has instructed to interrupt the display of the currently displayed medical image and to display a next medical image. The instruction 520 for image designation is constituted of buttons of "FORWARD", "REVERSE" and "LIST", and a depression of the "FORWARD" button designates a next medical image. The sequence proceeds to step S408 or S405 respectively according as the display of a next medical image is instructed or not.

Step S405: There is discriminated whether the image reading person has instructed to interrupt the display of the currently displayed medical image and to display a preceding medical image. A depression of the "REVERSE" button in the instruction 520 for image designation designates a preceding medical image. The sequence proceeds to step S409 or S406 respectively according as the display of a previous medical image is instructed or not.

Step S406: There is discriminated whether the image reading person has instructed to interrupt the display of the currently displayed medical image and to display a list of subjects. A depression of the "LIST" button in the instruction 520 for image designation designates a display of a list of the subjects. The sequence proceeds to step S407 or S411 respectively according as the display of a list of the subjects is instructed or not.

Step S407: A list of persons who take inspections (subjects) is displayed, and the sequence proceeds to step S410.

Step S408: In case a display of a next medical image is instructed despite that the current medical image is the last medical image, there is displayed a message of such effect and the sequence returns to step S402.

Step S409: In case a display of a preceding medical image is instructed despite that the current medical image is the first medical image, there is displayed a message of such effect and the sequence returns to step S402.

Step S410: There is discriminated whether the image reading person has designated a subject in the list of the subject displayed in step S407. In a case where a subject is designated, a medical image number i thereof is acquired and the sequence returns to step S402. If the subject is not designated, there is discriminated whether a change in the display mode for the currently displayed medical image. In the image display mode, there can be executed an image scaling-up, a scaling-down, a contrast adjustment and a distance measurement, and there can also be set a step s. The sequence proceeds to step S412 or S413 respectively according as a change in the display mode is instructed or not.

Step S411: a change in the display mode is executed. An instruction for the change of the display mode is constituted of an image scale-up/down button 530, a contrast adjustment button 540 and a distance measurement button 550. In the image scale-up/down button 530, a depression of a rightward arrow button or a leftward arrow button respectively causes an enlargement or a reduction of the image. Also, in the contrast adjustment button 540, a depression of a rightward arrow button or a leftward arrow button respectively causes an increase or a decrease in the contrast. A depression of the distance measurement instruction button 550 executes a distance measurement. In a step designation area, there are provided a window 542 for displaying a current step and increase/decrease arrows 544, and a depression of an upward arrow increases the step and an increased step is displayed in the window 542. Also a depression of a downward arrow decreases the step and a decreased step is displayed in the window 542.

Then the sequence proceeds to step S412:

Step S412: There is executed a change in the display mode designated in step S411;

Step S413: There is discriminated whether an image reading time, of which counting was started in step S403 has expired. The sequence proceeds to step S414 or returns to step S404 respectively in case the image reading time has expired or not;

Step S414: There is discriminated, on the currently displayed medical image, whether a result of image reading has been inputted (not suspended). The sequence proceeds to step S421 or S415 respectively in case the result of image reading has been inputted (not suspended) or not;

Step S415: An input image for inputting a result of image reading is displayed. By automatically displaying an input image at the expiration of the image reading time in this manner, it is possible to alleviate the burden on the image reading person and to prevent a lapse in the input. By providing a certain voice message simultaneously with the display of the input image, it is possible to enhance the effect of preventing a lapse in the input.

As shown in FIG. 13, the input image includes a medical image display area 600, a subject data display area 610, a detailed information input area 620, a sound input designation button 630, a hold selection button 640 and a standard document selection area 650.

Then the sequence proceeds to step S416:

Step S416: A timer for measuring an image reading result input waiting time is started;

Step S417: There is discriminated whether the image reading person has selected a suspension of the image reading result. The suspension is selected by depressing the hold button 640. The sequence proceeds to step S421 or S418 respectively in case the suspension is selected or not;

Step S418: There is discriminated whether the image reading person has inputted a result of image reading. The image reading result can be inputted by entering a text in the detailed information input area 620, or by executing a sound input under a depression of the sound input designation button 630, or by selecting a standard document in the standard document selecting area 650. A standard document can be selected by various methods, for example by selecting a standard document from a pull-down menu, or by suitably scrolling standard documents displayed in the display area 652 by a scroll button 654.

The sequence proceeds to step S421 or S419 respectively in case the result of image reading is inputted or not:

Step S419: There is discriminated whether a waiting time for input of the result of image reading has expired. The sequence proceeds to step S420 or returns to step S417 respectively according as the waiting time for input of the result of image reading has expired or not;

Step S420: A state in which the waiting time for input of the result of image reading has expired without the input is regarded as a suspension and the sequence proceeds to step S421. In this manner there can be prevented a lapse in the input;

Step S421: There is designated a medical image advanced by the internal s of the medical images, whereby the images are advanced automatically to alleviate the burden of the image reading person. Particularly in case of browsing all the images without entering the result of image reading, the image reading person can execute such browsing without any operation, whereby the burden of the image reading person can be significantly reduced;

Step S422: There is discriminated whether the image reading of the medical image has been completed, and the sequence is terminated or returns to step S402 respectively according as the image reading is completed or not.

The fourth embodiment provides a suspension process, thereby enabling the image reading person to input the result of image reading at an arbitrary timing and to prevent a lapse in the input.

Fifth Embodiment

In the following, a fifth embodiment of the present invention will be explained in detail with reference to accompanying drawings.

Recently CAD of various types are conceived depending on an image or an object to be considered, but a CAD for obtaining a difference of images of a same site thereby forming an image emphasized in a change in time is attracting attention.

In a medical facility utilizing such CAD, it has been common to compare two images different in time on a light box or the like, in order to judge a proceeding of a disease or a progress in a treatment.

However, since the digital image pickup has become possible as explained in the foregoing, it is conceived possible, for example, to execute an image analysis on a set of simple chest X-ray images taken at different times thereby determining an anatomically same position in each image, and to deform either one of the present image or the past image thereby executing a differential process on each pixel.

A density value of the image obtained by such differential process (differential process) corresponds to a difference in the image signal between the present and past images. More specifically, the differential between these images becomes zero in case the present image and the past image show no change, but, in case there is any variation between the present image and the past image, the luminance level shows a change corresponding to such variation.

A judgment with such differential image can clearly and positively indicate a progress in the treatment or a proceeding in the disease in comparison with a judgment of such progress of the treatment or the proceeding of the disease based on a mere comparison of the past and present images in human brain, and a display of such differential image is very effective means for preventing an erroneous diagnosis or an error in the judgment of a doctor.

For example, in case there are three or more images different in time, there can be generated plural differential images, thereby allowing to more exactly know a change in the image over a prolonged period.

FIG. 14 is a block diagram showing a configuration of a medical image handling system of the present embodiment.

Referring to FIG. 14, there are provided image reading means 1101, image processing means 1102, image display means 1103, divided display format setting means 1104, display mode setting means 1105, image switching means 1106, taken images 1107, diagnosis supporting images 1108, and a monitor 1109. In the present embodiment, it is assumed that the taken images 1107 and the diagnosis supporting images 1108 are already stored in the memory media.

Figure 15:
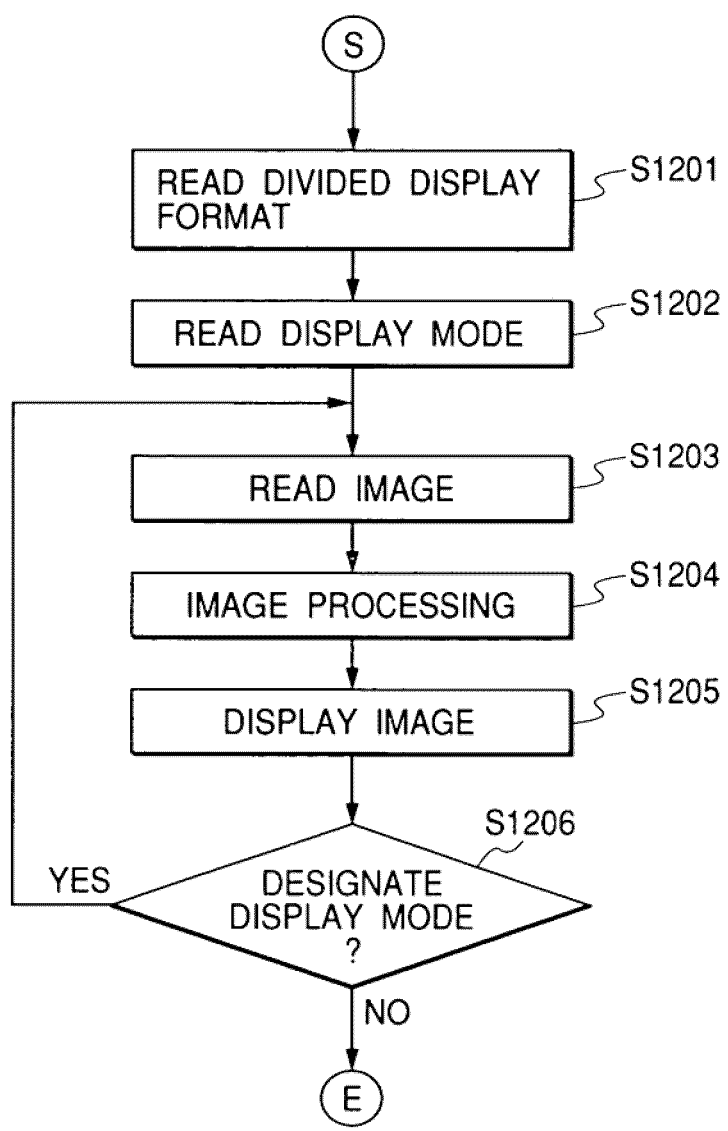
FIG. 15 shows the fifth embodiment and is a flow chart showing a function of the medical image handling system.

In the following, there will be explained a function and an operation of the medical image handling system of the present embodiment, constructed as explained above. FIG. 15 is a flow chart for switching a display of a taken image and a diagnosis supporting image, based on an instruction for changing a display mode setting.

At first in step S1201, the image reading means 1101 reads a set value of a divided display image format. The divided display image format includes, for example, a single image display, a left-right two-image display, an upper-lower two-image display, a four-image display and a display of more images, and is selected according to an operator operation utilizing the divided display format setting means 1104.

The images displayed in the respective image display areas are those of a same subject, distanced in time. The medical image is usually displayed according to a DICOM (digital and communication medicine) standard.

According to the DICOM standard, each of the images distant in time is called a study. Therefore each patient has plural studies different in time.

Then, in step S1202, the image reading means 1101 reads a display mode for each study. The display mode is set based on an operation of the operator utilizing the display mode setting means 1105, and, in the present embodiment, includes a mode of displaying a taken image and a mode of displaying a diagnosis supporting image.

The diagnosis supporting image is for example a time-differential image, but such example is not restrictive and there may be employed any image capable of supporting the diagnosis of the image reading doctor.

Then, in step S1203, the image reading means 1101 reads image data. More specifically, the image reading means 1101 reads necessary image data according to set values, set in steps S1201 and S1202.

For example, in a case of a divided display format for displaying taken images both at right and left, there are read, among the studies of the patient, image data of a most recent study and those of a study preceding to the most recent study.

Also, in a case where the divided display format is for displaying two left-right images and a display mode for the left image display area is a mode for displaying a taken image and a display mode for the right image display area is a mode for displaying a diagnosis supporting image, there are read, among the studies of the patient, a most recent study and an image of a difference between the most recent study and a study preceding the most recent study, namely a time-differential image between the present image and the immediately preceding image.

Then, in step S1204, the image processing means 1102 executes an image processing on the image data read in step S1203. Usually it is possible, by selecting the divided display format, to acquire and determine a size of each image display area, a gamma value of the monitor, a lookup table for display, and a displayed image size.

Then, based on these parameters, an image processing is executed on the image data read in step S1203. However, the parameters acquired and determined in step S1204 are not limited to those mentioned above.

Then, in step S1205, the image display means 1103 displays, on a monitor 1109, an image subjected to the image processing in step S1204. The image displayed on the monitor 1109 is read usually by an image reading doctor.

Then, in step S1206, the image reading means 1101 checks whether an instruction for changing the aforementioned display mode has been given from the operator. Such instruction for change is given by the operator, utilizing the image switching means 1106.

In a case where a change in the display mode is instructed, the image data to be displayed are determined according to such instruction. For this purpose, the S1203 reads the determined image data to be displayed, then step S1204 executes an image processing on the read image data, and step S1205 displays the image, subjected to such image processing, on the monitor 1109.

Figure 16:
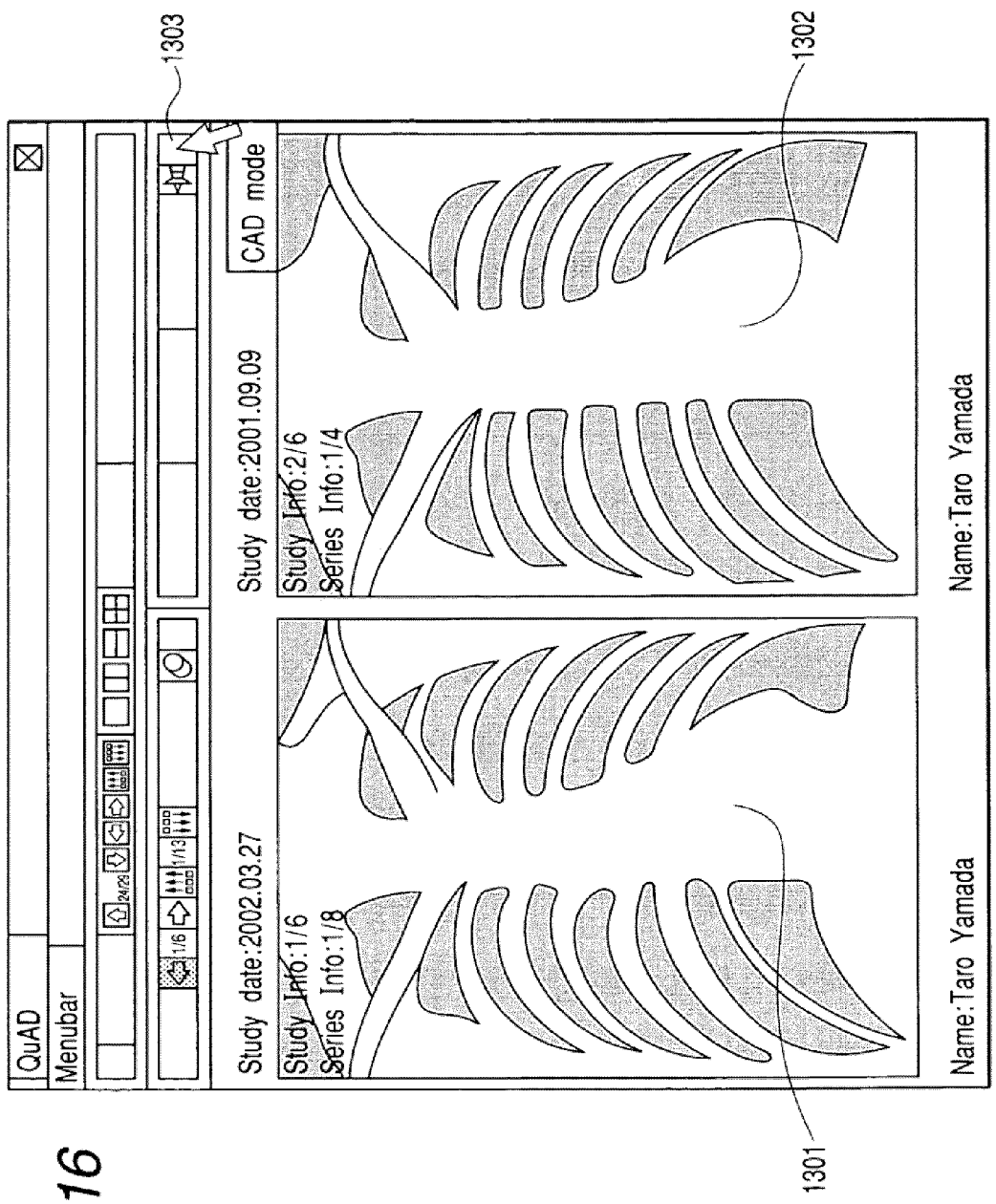
FIG. 16 shows the fifth embodiment and is a view showing an example of a display prior to a switching of a display mode.

The instruction for changing the display mode is executed, for example as shown in FIG. 16, by displaying a button 1303 for switching the display mode together with the images 1301, 1302 in the process of step S1205 and by depressing such button 1303 by an operator of the operator.

In FIG. 16, a symbol 1303 indicates a button for switching the display mode. However, operation means for switching the display mode is not limited to such button.

Also in FIG. 16, a symbol 1301 indicates a latest image of the patient, which in this example is a front chest image taken on Mar. 27, 2002. Also a symbol 1302 in FIG. 16 indicates an image which immediately precedes the latest image among images of a same site of the same patient, and which in this example is an image taken on Sep. 9, 2002. In this manner it is possible to compare the image taken at the present time and the image taken previously.

By clicking the button 1303 with a mouse, the display mode can be changed from a mode of displaying a taken image to a mode of displaying a time-differential image which is a diagnosis supporting image.

Figure 17:
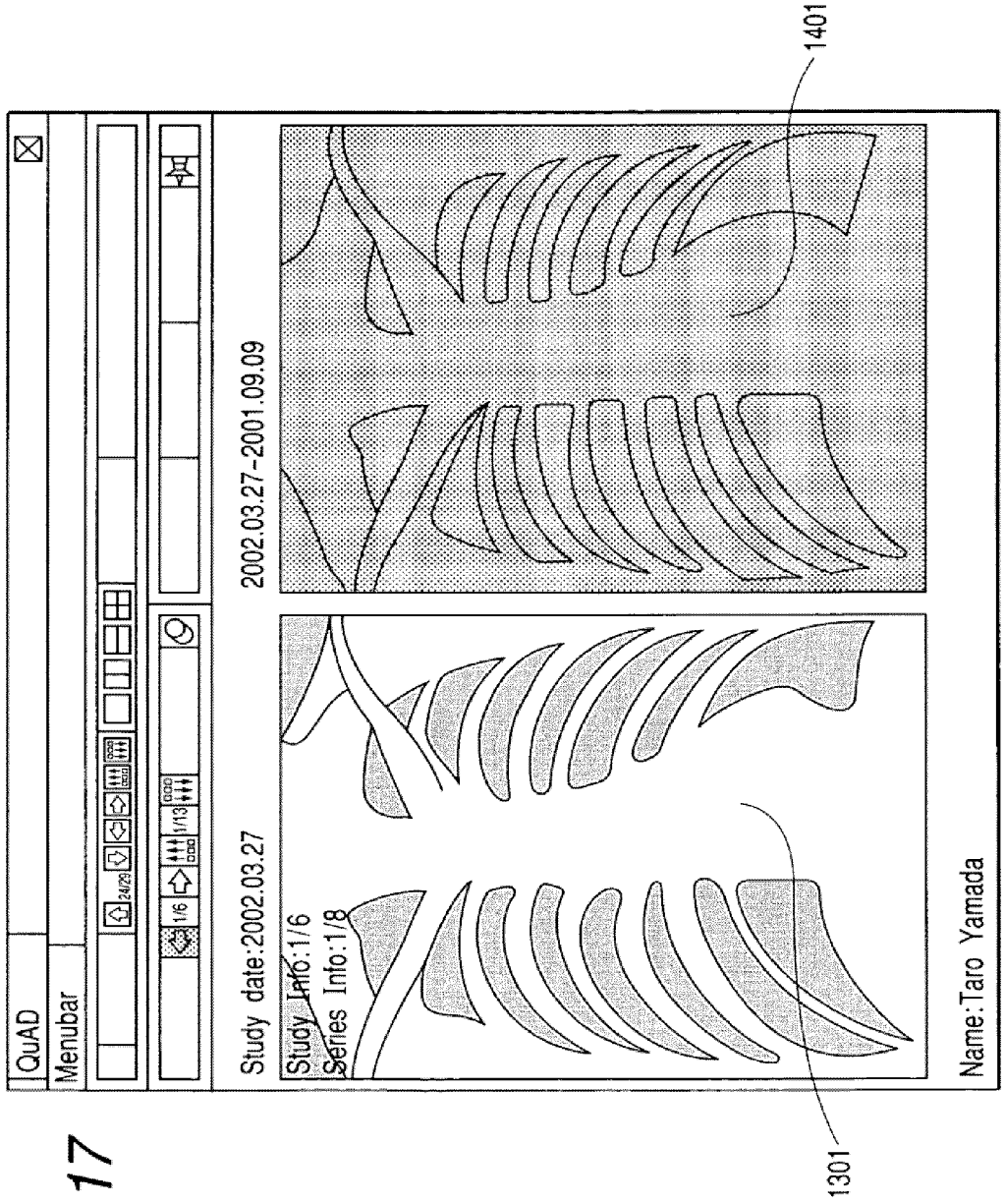
FIG. 17 shows the fifth embodiment and is a view showing an example of a display after a switching of a display mode.

When the button 1303 is clicked in the state shown in FIG. 16 to select the time-differential image display mode, a time-differential image is prepared from the latest image 1301 displayed in the left image display area and the image 1302 displayed in the right image display area. Then, as shown in FIG. 17, the latest image 1301 on the monitor 1109 is retained in the displayed state, and a time-differential image 1401, prepared from the latest image 1301 and the image 1302 immediately preceding the latest image, is displayed at a side of the latest image 1301.

In this manner the display mode is switched from the mode for displaying the taken image to the mode for displaying the diagnosis supporting image.

In the present embodiment, there is explained a case of executing the process by reading the images in succession, but, in the actual image reading site, it is preferable to pre-fetch the images since the image reading takes time.

Such pre-fetch is possible also in the present embodiment, but it is necessary to vary a priority of images to be pre-fetched according to the divided display format or the display mode.

FIG. 18 shows an example of the pre-fetching priority in a display mode of displaying the taken images.

In an example shown in FIG. 18, in case of a single-image (No division) display, into which a display area is divided, a priority is given in an order of a first series, a second series and a third series in a first study (study 1).

Also, in a case of a two-image (2-division) display, a priority is given in an order of a first series in an initial study (study 1), a first series in a second study (study 2), a second series in the initial study (study 1), and a third series in the initial study (study 1).

Also, in a case of a four-image (4-division) display, a priority is given in an order of a first series in an initial study (study 1), a first series in a second study (study 2), a first series in a third study (study 3), a first series in a fourth study (study 4), a second series in the initial study (study 1), and a third series in the initial study (study 1).

Also, FIG. 19 shows an example of the pre-fetching priority in a left-right two-division format.

In a case of displaying the taken images in left and right image portions of the monitor 1109, a priority is given, as shown in FIG. 19, in an order of a taken image in a first study (study 1), a taken image in a second study (study 2), a differential image of the taken image in the first study and the taken image in the second study (CAD study 1-study 2), a taken image in a third study (study 3), a taken image in a fourth study (study 4), a differential image of the taken image in the second study and the taken image in the third study (CAD study 2-study 3), and a differential image of the taken image in the third study and the taken image in the fourth study (CAD study 3-study 4).

Also, in a case of displaying a taken image in a left half image portion of the monitor 1109, and a diagnosis supporting image in a right half image portion, a priority is given in an order of a taken image in a first study (study 1), a differential image of the taken image in the first study and the taken image in the second study (CAD study 1-study 2), a taken image in a second study (study 2), a taken image in a third study (study 3), a taken image in a fourth study (study 4), a differential image of the taken image in the second study and the taken image in the third study (CAD study 2-study 3), and a differential image of the taken image in the third study and the taken image in the fourth study (CAD study 3-study 4).

As explained in the foregoing, the present embodiment sets at least an image display area in a divided display image format and also sets either of the taken image 1107 and the diagnosis supporting image (differential image) 1108 in thus set image display area thereby displaying the set image in the set image display area, whereby the taken image 1107 or the differential image 1108 can be displayed in an optimum form and the differential image 1108 can be referred to at the image reading within a same image frame displaying the taken image 1107.

Also, since there are set plural image display areas and the taken image 1107 and the diagnosis supporting image (differential image) 1108 are displayed in thus set plural image display areas, it is rendered possible to positively indicate the differential image 1108 simultaneous with a diseased part of the original taken image 1107, thereby allowing to promptly and securely understand the proceeding of the diseased part or the progress of the treatment between studies distanced in time, in comparison with the prior method in which the diseased part is understood by the doctor through a comparison of the taken images.

Also, the present embodiment, employing a CAD image as the diagnosis supporting image, allows to employ and display images of various forms as the diagnosis supporting image. In this manner, the image reading doctor can display a desired image and can derive a result of image reading by arbitrarily referring to various images.

Also, when the image reading doctor reads an image on a monitor or a film, a size or a shape of a diseased part may be unconsciously deformed in case a sight line is displaced from a point to be noticed. For this reason, the image reading doctor generally dislikes a large displacement of the sight line in the course of the image reading.

For example, in case of displaying images on two monitors and comparing the left and right images displayed on such two monitors, it is necessary, after reading the image displayed on a monitor, to move the slight line significantly to the other monitor. This may also interrupt the consideration of the doctor. Thus, in case of comparing two images, a displacement of the sight line from the point to be noticed may result in a deterioration of the image reading efficiency.

On the other hand, in the present embodiment, since the taken image and the diagnosis supporting image are displayed in a same (alternate) image display area, the image reading doctor can refer to the taken image and the diagnosis supporting image without a large displacement of the sight line. In this manner it is possible to improve the image reading efficiency. Particularly in case of comparing the size or the shape of the diseased part, the image reading doctor can make such comparison without interrupting the consideration, whereby a very significant effect can be obtained.

Also, in a case where the images are not pre-fetched, when the image reading doctor instructs the display of a desired image, there are executed a loading of the image and an optimum image processing before the image is displayed on the monitor, whereby the display has a poor response and the efficiency of diagnosis is significantly deteriorated.

On the other hand, in the present embodiment, since a priority of the images to be pre-fetched is determined according to the divided display format and the display mode (pre-fetching condition being switched), the images are read into the memory always in an optimum condition. Consequently, the image reading doctor can display a desired image on the monitor 1109 at a desired time, without interruption of the consideration, thereby an improvement is achieved in the efficiency of image diagnosis and also in the precision of diagnosis.

Sixth Embodiment

In the following, a sixth embodiment of the present embodiment will be explained in detail. This embodiment is different from the fifth embodiment in a process in case an instruction for switching the image is given. Therefore portions that are the same as those in the foregoing fifth embodiment are indicated by symbols same as those in FIGS. 14 to 19 and detailed explanations on these portions will be omitted.

Figure 20:
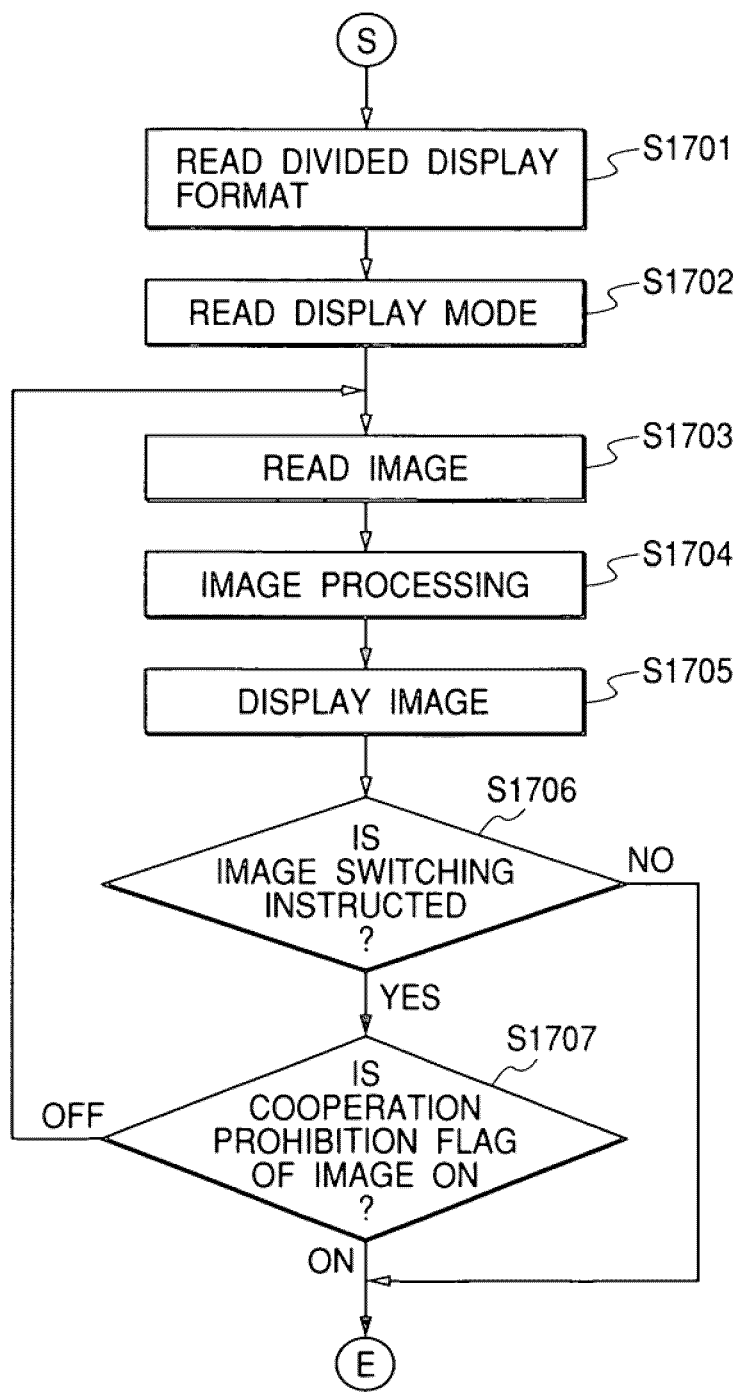
FIG. 20 shows a sixth embodiment and is a flow chart showing a function of a medical image handling system.

In the following, there will be explained a function and an operation of the medical image handling system of the present embodiment, with reference to FIG. 20. FIG. 20 is a flow chart for, in a case of an instruction for changing a taken image from the operator, switching the diagnosis supporting image in linkage.

Steps S1701 to S1705 are the same as steps S1201 to S1205 of the foregoing fifth embodiment explained in FIG. 15, and will not, therefore, be explained further.

In step S1706, the image reading means 1101 discriminates whether an image switching is instructed from the operator. The sequence proceeds to step S1707 or is terminated respectively in case the instruction for the image switching is present or absent.

In the following a specific operation for the image switching will be explained. As an example, FIG. 21 shows a case where the divided image format is a left-right two division, in which the left image display area is set at a mode of displaying a taken image and the right image display area is set at a mode of displaying a diagnosis supporting image.

Figure 21:
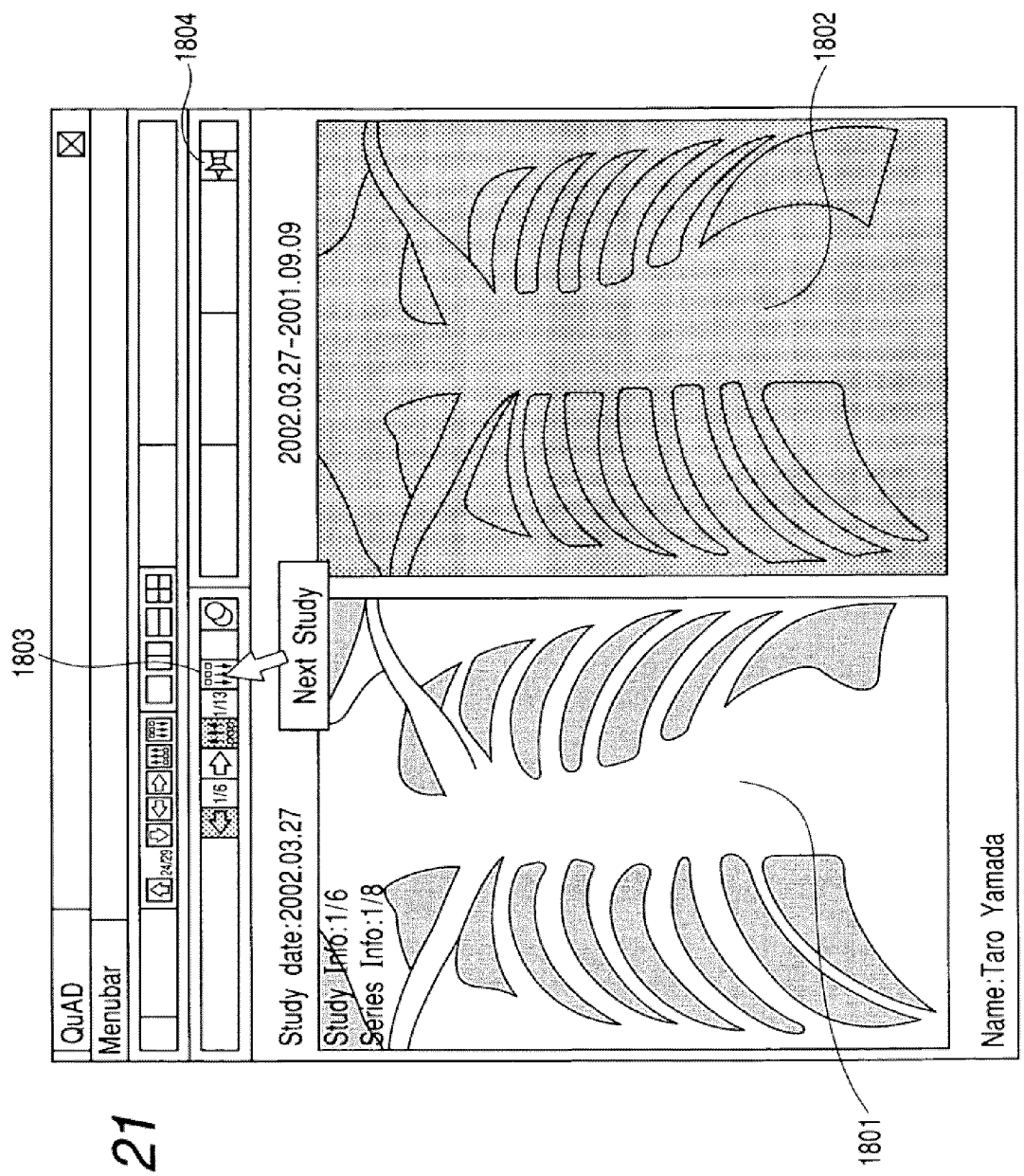
FIG. 21 shows the sixth embodiment and is a view showing an example of display prior to a switching of an image.

In FIG. 21, a symbol 1803 indicates an image switching button. An image switching instruction is generated by clicking of the image switching button 1803 with a mouse by the operator.

In step S1707, the image reading means 1101 discriminates whether a link inhibition flag is turned on or off. The sequence is terminated in case the link inhibition flag is on, but, in case the link inhibition flag is off, the sequence returns to step S1703 to read a next image and step S1704 to execute the image processing, and step S1705 displays a next image.

In the following, there will be explained a specific operation of the link inhibition flag. In FIG. 21, the link inhibition flag is turned on/off by a depression of a link inhibition flag setting button 1804 by the operator. However a method for on/off switching of the link inhibition flag is not limited to such example.

In FIG. 21, the link inhibition flag is turned off.

Therefore, the diagnosis supporting image is switched in linkage with an image switching instruction of the operator in step S1706.

On the other hand, in a case where the link inhibition flag is turned on, when an image switching instruction is given in step S1706, the diagnosis supporting image is prevented from switching and retains a state before the switching instruction.

Such image switching operation will be explained with reference to FIG. 21. FIG. 21 shows a state before the image switching instruction is given. In FIG. 21, a taken image 2801, which is a latest study of the patient, taken on Mar. 27, 2002, is displayed in the left image display area.

Also, the right image display area displays a time-differential image as a diagnosis supporting image. In this example, there is displayed a time-differential image prepared from an image taken in a study on Mar. 27, 2002 and an image taken in a study on Sep. 9, 2001.

Figure 22:
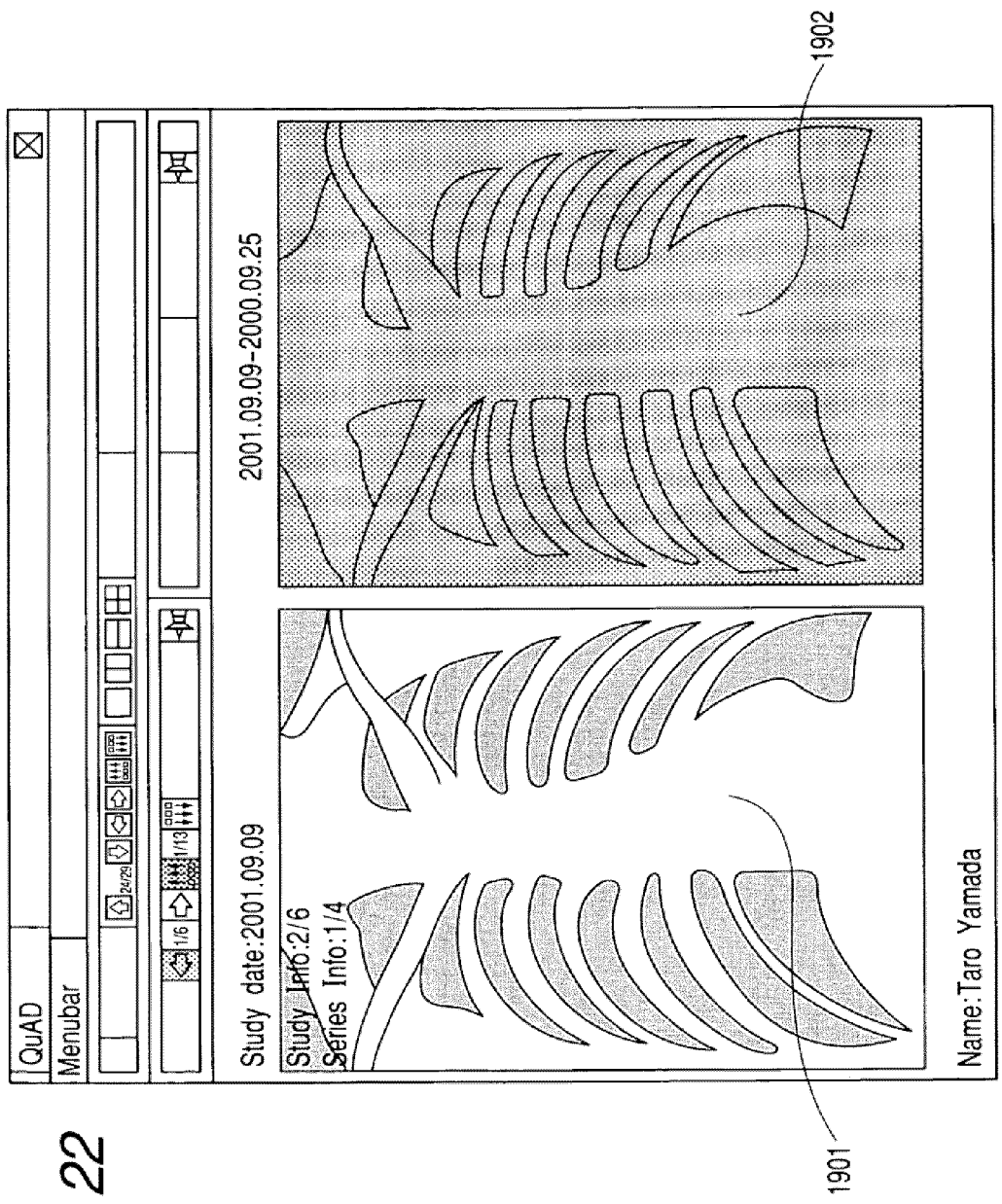
FIG. 22 shows the sixth embodiment and is a view showing an example of display after a switching of an image.

In a case where the operator clicks the image switching button 1803 with the mouse while these images are displays, the two images displayed in the left and right image display areas are switched in linkage. FIG. 22 shows a state after the left and right two images are switched in linkage by the clicking of the image switching button 1803. The taken image 1801 of the latest study, displayed in the left image display area in FIG. 21, is switched to a taken image 1901 taken in a study of Sep. 9, 2001, immediately preceding the latest study.

Also, the diagnosis supporting image displayed in the right image display area in FIG. 22 is switched in linkage with the taken image displayed in the left image display area.

Stated differently, in the state shown in FIG. 21, the left image display area displays the taken image 1801 obtained in the study of Mar. 27, 2002, and the right image display area displays the time-differential image of the image of Mar. 27, 2002, and the image of Sep. 9, 2001. In FIG. 22 after the switching, the left image display area displays the taken image 1901 obtained in the study of Sep. 9, 2001, and the right image display area displays the time-differential image of the image of Sep. 9, 2001, and the image of Sep. 25, 2000. The image of Sep. 25, 2000, is an image taken in a study preceding the image of Sep. 9, 2001. Therefore, this image was taken in a second study before the latest image.

Thus, this patient was subjected to front chest X-ray imaging on Mar. 27, 2002, Sep. 9, 2001, and Sep. 25, 2000. Therefore, at the observation of the image of Mar. 27, 2002, there is simultaneously displayed a time-differential image prepared from the image of Sep. 9, 2001, which is immediately preceding (older than) the image of Mar. 27, 2002, and the image of Mar. 27, 2002, and, at the observation of the image of Sep. 9, 2001, there is simultaneously displayed a time-differential image prepared from the image of Sep. 25, 2000, which is immediately preceding (older than) the image of Sep. 9, 2001, and the image of Sep. 9, 2001.

In the present embodiment, as explained in the foregoing, in a state where the taken image 1801 in the latest study is displayed in the left image display area and the time-differential image 1802, prepared from the taken image 1801 in the latest study and the taken image in the immediately preceding study, is displayed in the right image display area, when the taken image 1801 is switched to the taken image 1901 taken in an immediately preceding study, the time-differential image displayed in the right image display area is also switched in linkage to a time-differential image 1902 prepared from the taken image in a study immediately preceding the latest study and the taken image in a study second preceding the latest study.

Thus, since, at the switching of the taken image, the diagnosis supporting image is switched in linkage with such switching of the taken image, the taken image and the diagnosis supporting image can always be displayed as a pair of images. The relationship between the taken image and the diagnosis supporting image can be understood more easily.

For example, in a case where each of the taken image and the time-differential image (diagnosis supporting image) is present in plural units, such time-differential images are very similar, so that it is very difficult, in a mere display of a time-differential image, to immediately identify such time-differential image is obtained from which ones of the taken images.

Also, it has not been possible to switch the display of a first taken image, a second taken image and a third taken image, a differential image of the first taken image and the second taken image, and a differential image of the second taken image and the third taken image, so that a correspondence between a taken image and a time-differential image (diagnosis supporting image) has been difficult to understand.

In contrast, the present embodiment switches the time-differential image (diagnosis supporting image) in linkage with a switching operation of the taken image, thereby enabling to display the taken image and the diagnosis supporting image in a pair and to immediately understand the nature of the time-differential image (diagnosis supporting image).

Figure 23:
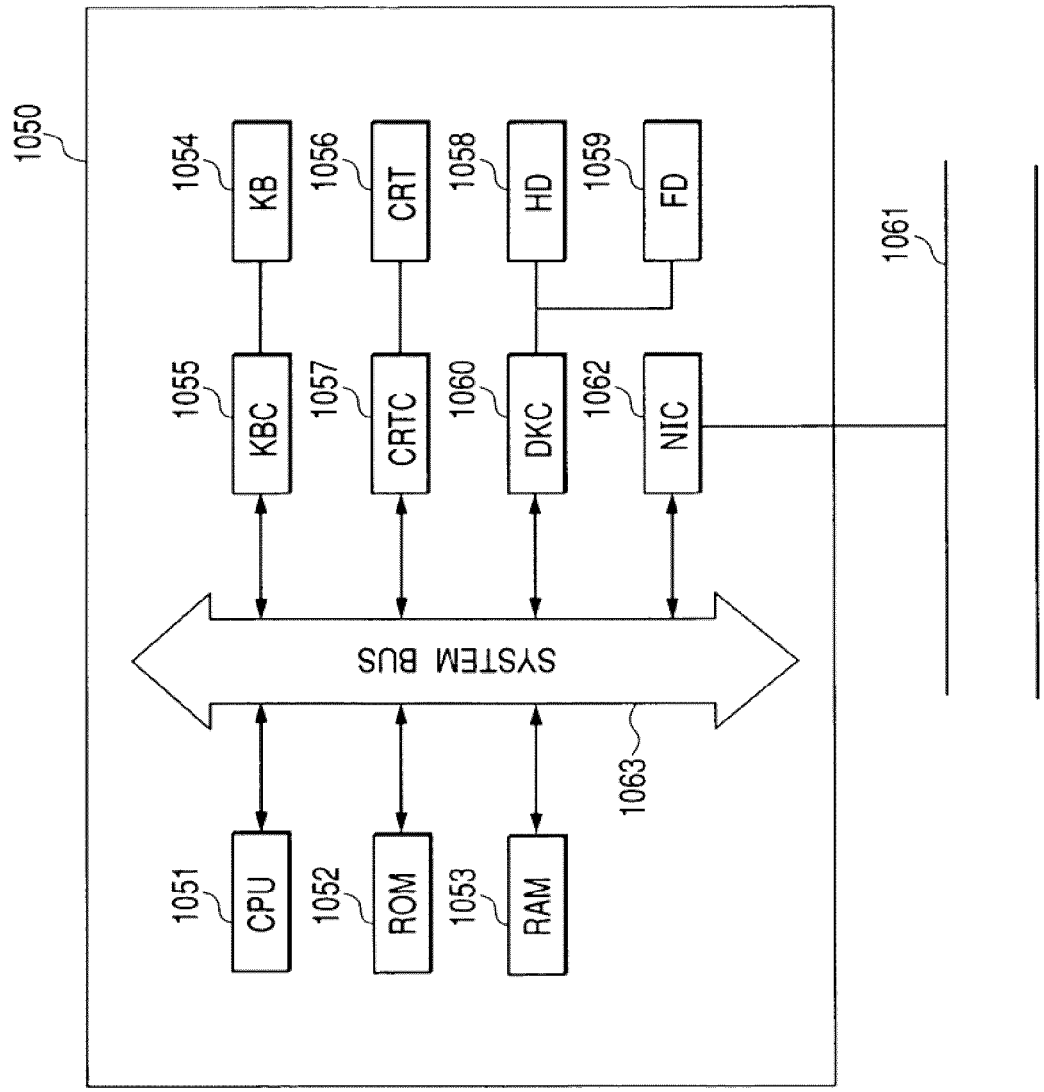
FIG. 23 shows an embodiment of the present invention and is a block diagram of an example of a configuration of a computer system provided in the medical image handling system.

The medical image handling system explained in the foregoing embodiments can be realized by a computer system as shown in FIG. 23.

FIG. 23 is a block diagram showing an example of a computer system provided in the medical image handling system.

In FIG. 23, a computer system 1050 is constituted of a CPU 1051, a ROM 1052, a RAM 1053, a keyboard controller (KBC) 1055 for a keyboard (KB) 1054, a CRT controller (CRTC) 1057 for a CRT display (CRT) 1056 constituting a display unit, a disk controller (DKC) 1060 for a hard disk (HD) 1058 and a flexible disk (FD) 1059, and a network interface controller (NIC) 1062 for a network 1061, connected through a system bus 1063 in mutually communicable manner.

The CPU 1051 collectively controls the components connected to the system bus 1053 by executing a software stored in the ROM 1052 or the HD 1058, or a software supplied from the FD 1029.

Thus the CPU 1051 executes control for realizing following operations, by reading and executing a program of predetermined process sequence from the ROM 1052, the HD 1058, or the ED 1029.

The RAM 1053 functions as a main memory or a work area of the CPU 1051. The KBC 1055 controls an instructing input from an unrepresented pointing device or the like.

The CRTC 1057 controls a display on the CRT 1056.

The DKC 1060 controls an access to the HD 1058 and the FD 1059, storing a boot program, various applications, an editing file, a user file, a network management program, and predetermined processing programs in the present embodiment. The NIC 1052 executes bidirectional data exchange with an apparatus or a system on the network 1061.

Other Embodiments of the Present Invention

The present invention also includes a case of supplying a computer in an apparatus or a system connected with various aforementioned devices so as to operate these devices for realizing the functions of the aforementioned embodiments, with program codes of a software realizing the functions of the aforementioned embodiments, and operating the various devices according to the program stored in the computer (or CPU or MPU) of such system or apparatus.

In such a case, the program codes themselves of the program realize the functions of the aforementioned embodiments, and the program codes themselves or means for supplying such program codes to the computer, such as a memory medium storing the program codes, constitute the present invention. The memory medium storing such program codes can be, for example, a flexible disk, a hard disk, an optical disk, a magnetooptical disk, a CD-ROM, a magnetic tape, a non-volatile memory card or a ROM.

Such program codes are naturally included in embodiments of the present invention not only in a case where the computer executes the supplied program codes to realize the functions of the aforementioned embodiments but also a case where the program codes realize the functions of the aforementioned embodiments in cooperation with an OS (operating system) or another application functioning on the computer.

Furthermore, the present invention includes a case where the supplied program codes are once stored in a memory provided in a function expansion board of the computer or a function expansion unit connected to the computer, and a CPU or the like provided in such function expansion board or function expansion unit executes all the actual processes or a part thereof based on the instruction of the program codes, thereby realizing the function of the aforementioned embodiments.

What is claimed is:

1. A medical image handling system, comprising:
    an image display unit adapted to display a taken image and a time-differential image corresponding to the taken image on an image frame of a monitor; and
    an image switching unit adapted to, in case of switching the taken image to be displayed by said image display unit from a first taken image to a second taken image, switch the time-differential image to be displayed by said image display unit from the time-differential image corresponding to the first taken image to the time-differential image corresponding to the second taken image in linkage with the switching from the first taken image to the second taken image,
    wherein, in a case where a link inhibition flag is off, the taken image is switched by the image switching unit and the time-differential image is switched by the image switching unit in linkage with the switching of the taken image in response to a switching instruction for the taken image, and
    in a case where the link inhibition flag is on, only the taken image is switched by the image switching unit but the time-differential image is inhibited from being switched even if the switching instruction for the taken image is issued.

2. A medical image handling method, comprising the steps of:
    displaying a taken image and a time-differential image corresponding to the taken image on an image frame of a monitor; and
    in case of switching the taken image to be displayed on the monitor from a first taken image to a second taken image, switching the time-differential image to be displayed on the monitor from the time-differential image corresponding to the first taken image to the time-differential image corresponding to the second taken image in linkage with the switching from the first taken image to the second taken image,
    wherein, in a case where a link inhibition flag is off, the taken image is switched and the time-differential image is switched in linkage with the switching of the taken image in response to a switching instruction for the taken image, and
    in a case where the link inhibition flag is on, only the taken image is switched but the time-differential image is inhibited from being switched even if the switching instruction for the taken image is issued.

3. The medical image handling system according to claim 1, further comprising a restriction unit adapted to restrict the switching of said image switching unit on the basis of a user instruction.

4. The medical image handling method according to claim 2, further comprising restricting the switching of the display of the time-differential image on the basis of a user instruction.

5. A medical image handling system, comprising:
    an image display unit adapted to display a taken image and a time-differential image corresponding to the taken image on an image frame of a monitor; and
    an image switching unit adapted to switch display of the taken image and the time-differential image on the monitor,
    wherein, in a case where the taken image taken in a latest inspection is switched by said image switching unit to the taken image taken in a most-recent previous inspection in a state in which the time-differential image obtained between the taken image taken in the latest inspection and the taken image taken in the most-recent previous inspection is being displayed by said image switching unit, the time-differential image obtained between the taken image taken in the most-recent previous inspection and the taken image taken in a second-most-recent previous inspection is displayed by said image switching unit, in linkage with said switching,
    in a case where a link inhibition flag is off, the taken image is switched by the image switching unit and the time-differential image is switched by the image switching unit in linkage with the switching of the taken image in response to a switching instruction for the taken image, and
    in a case where the link inhibition flag is on, only the taken image is switched by the image switching unit but the time-differential image is inhibited from being switched even if the switching instruction for the taken image is issued.

6. A medical image handling method which is applied to a medical image handling system including a monitor, comprising:
    an image display step of displaying a taken image and a time-differential image corresponding to the taken image on an image frame of the monitor; and
    an image switching step of switching display of the taken image and the time-differential image on the monitor,
    wherein, in a case where the taken image taken in a latest inspection is switched in the image switching step to the taken image taken in a most-recent previous inspection in a state in which the time-differential image obtained between the taken image taken in the latest inspection and the taken image taken in the most-recent previous inspection is being displayed in the image switching step, the time-differential image obtained between the taken image taken in the most-recent previous inspection and the taken image taken in a second-most-recent previous inspection is displayed in the image switching step, in linkage with said switching,
    in a case where a link inhibition flag is off, the taken image is switched in the image switching step and the time-differential image is switched in the image switching step in linkage with the switching of the taken image in response to a switching instruction for the taken image, and
    in a case where the link inhibition flag is on, only the taken image is switched in the image switching step but the time-differential image is inhibited from being switched even if the switching instruction for the taken image is issued.

7. A medical image handling apparatus, comprising:
    an image display control unit adapted to control to display a taken image and a time-differential image corresponding to the taken image on a frame of a monitor; and
    an image switching unit adapted to, in case of switching the taken image to be displayed by said image display control unit from a first taken image to a second taken image, switch the time-differential image to be displayed by said image display control unit from the time-differential image corresponding to the first taken image to the time-differential image corresponding to the second taken image in linkage with the switching from the first taken image to the second taken image, wherein, when a link inhibition is not implemented, the taken image is switched by the image switching unit and the time-differential image is switched by the image switching unit in linkage with the switching of the taken image in response to a switching instruction for the taken image, and when the link inhibition is implemented, the taken image is switched by the image switching unit but the time-differential image is inhibited from being switched even if the switching instruction for the taken image is issued.

8. The medical image handling system according to claim 7, further comprising a restriction unit adapted to restrict the switching of said image switching unit on the basis of a user instruction.

9. A medical image handling method, comprising the steps of:

controlling to display a taken image and a time-differential image corresponding to the taken image on a frame of a monitor; and in a case of switching the taken image to be displayed from a first taken image to a second taken image, switching the time-differential image to be displayed from the time-differential image corresponding to the first taken image to the time-differential image corresponding to the second taken image in linkage with the switching from the first taken image to the second taken image, wherein, when a link inhibition is not implemented, the taken image is switched in said switching step and the time-differential image is switched in said switching step in linkage with the switching of the taken image in response to a switching instruction for the taken image, and when the link inhibition is implemented, the taken image is switched in said switching step but the time-differential image is inhibited from being switched even if the switching instruction for the taken image is issued.

10. The medical image handling method according to claim 9, further comprising the step of restricting the switching of the display of the time-differential image on the basis of a user instruction.

* * * * *